(12) United States Patent
Takahashi

(10) Patent No.: US 7,989,163 B2
(45) Date of Patent: Aug. 2, 2011

(54) DETECTION METHOD AND DETECTION APPARATUS OF SUBSTANCE IN BIOLOGICAL SAMPLE

(75) Inventor: Satoshi Takahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/100,570

(22) Filed: Apr. 7, 2005

(65) Prior Publication Data

US 2005/0227274 A1    Oct. 13, 2005

(30) Foreign Application Priority Data

Apr. 9, 2004   (JP) ................. 2004-115189

(51) Int. Cl.
| | |
|---|---|
| C12Q 1/68 | (2006.01) |
| G01N 33/53 | (2006.01) |
| C12M 1/00 | (2006.01) |
| G01J 3/30 | (2006.01) |
| C07H 21/02 | (2006.01) |
| C07H 21/04 | (2006.01) |

(52) U.S. Cl. .......... 435/6; 356/317; 435/7.1; 435/283.1; 536/23.1; 536/24.5

(58) Field of Classification Search ............... 435/6, 7.1, 435/283.1; 536/23.1, 24.5; 356/317
See application file for complete search history.

(56) References Cited

U.S. PATENT DOCUMENTS

| | | | | |
|---|---|---|---|---|
| 5,408,307 A | * | 4/1995 | Yamamoto et al. | ............ 356/73 |
| 5,601,983 A | * | 2/1997 | Takayama et al. | ............ 435/6 |
| 6,083,763 A | * | 7/2000 | Balch | ............ 436/518 |
| 6,490,533 B2 | * | 12/2002 | Weiner et al. | ............ 702/27 |
| 2002/0150925 A1 | * | 10/2002 | Chen et al. | ............ 435/6 |
| 2003/0087282 A1 | * | 5/2003 | Oshida et al. | ............ 435/6 |
| 2004/0132196 A1 | * | 7/2004 | Mizukami et al. | ............ 436/63 |
| 2004/0229245 A1 | * | 11/2004 | Bittner et al. | ............ 435/6 |
| 2005/0095172 A1 | | 5/2005 | Nagaoka et al. | |
| 2006/0035220 A1 | * | 2/2006 | Tashiro et al. | ............ 435/6 |

FOREIGN PATENT DOCUMENTS

| | | |
|---|---|---|
| EP | 1 347 285 | 9/2003 |
| JP | 2001-108684 | 4/2001 |
| WO | WO-03/009010 | 1/2003 |
| WO | WO-03/059484 | 7/2003 |

OTHER PUBLICATIONS

Van Elden et al, Simultaneous detection of influenza viruses A and B using real time quantitative PCR, 2001, J. clinical microbiology, 39, 196-200.*
Shapiro, Flow cytometric estimation of DNA and RNA content in intact cells staind with Hoechst 33342 and Pyronin Y, 1981, 2, 143-150.*

\* cited by examiner

*Primary Examiner* — Stephen Kapushoc
*Assistant Examiner* — Narayan K Bhat
(74) *Attorney, Agent, or Firm* — Dickstein Shapiro LLP

(57) ABSTRACT

A high accuracy method for detecting a biological-related substance is provided by which an abnormal state, such as the adhesion of dust, the reduction of a sample solution, or the like can be judged. Means for detecting a light emitted by the portion for light detection after dividing the light into at least a plurality of wavelength zones is provided. One of the plurality of wavelength zones includes substantially the same wavelength zone as that of the component of the excitation light. The light intensity of the component of the excitation light is detected and it is compared with a predetermined intensity (threshold). A highly accurate fluorescence measurement can be realized, by which the abnormality of a sample can be judged.

16 Claims, 20 Drawing Sheets

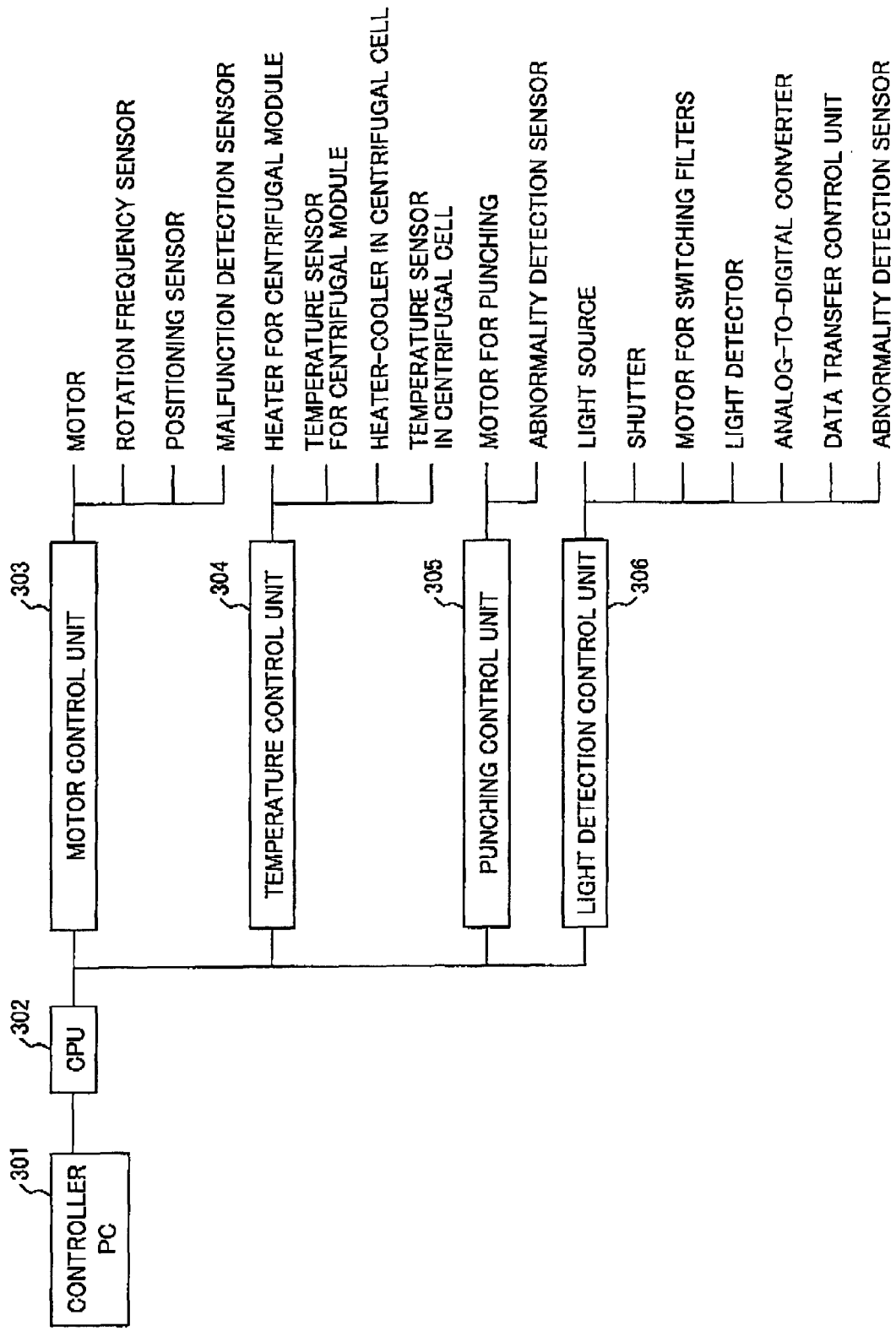

FILTER CHARACTERISTICS ARE ADJUSTED SUCH THAT DETECTED INTENSITY OF FLUORESCENCE AND DETECTED INTENSITY OF SCATTERED LIGHT ARE ABOUT THE SAME.

TO DETECTION PROCESS (IN STRUCTURE OF CENTRIFUGAL MODULE, PORTIONS IRRELEVANT TO PRESENT PROCESS ARE OMITTED)

FIG. 9 A 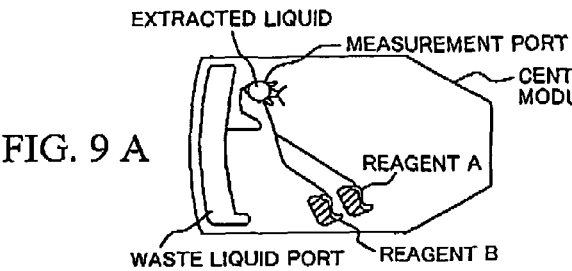

EXTRACT TARGET COMPONENT TO MEASUREMENT PORT IN ACCORDANCE WITH CONVENTIONAL METHOD.

REAGENT FOR AMPLIFICATION/ DETECTION IS ENCAPSULATED IN REAGENT A AND B PORTS.

FIG. 9 B 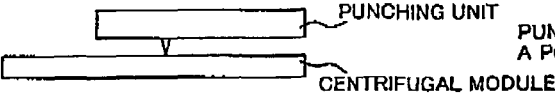

PUNCH UPPER PORTION OF REAGENT A PORT VIA PUNCHING UNIT.

FIG. 9 C   ROTATION (MIXTURE VIA CENTRIFUGAL FORCE), STOP

FIG. 9 D 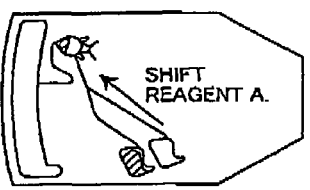

SHIFT REAGENT A TO MEASUREMENT PORT VIA CENTRIFUGAL FORCE AND MIX IT WITH EXTRACTED LIQUID.

FIG. 9 E   WARM TO 65°C. MAINTAIN FOR FIVE MINUTES.

FIG. 9 F   WORMING END. COOL TO NOT MORE THAN 40°C.

FIG. 9 G 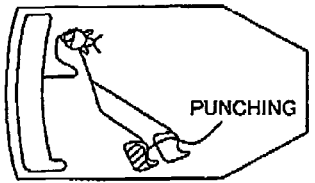

PUNCH UPPER PORTION OF REAGENT B PORT VIA PUNCHING UNIT.

FIG. 9 H   ROTATION (MIXTURE VIA CENTRIFUGAL FORCE), STOP

FIG. 9 I 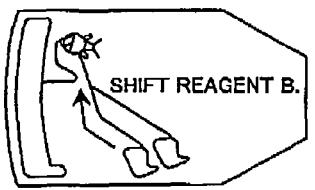

SHIFT REAGENT B TO MEASUREMENT PORT VIA CENTRIFUGAL FORCE AND MIX.

FIG. 9 J   WARM TO 41°C, MAINTAIN.

FIG. 9 K   CONDUCT LIGHT DETECTION PROCESS.

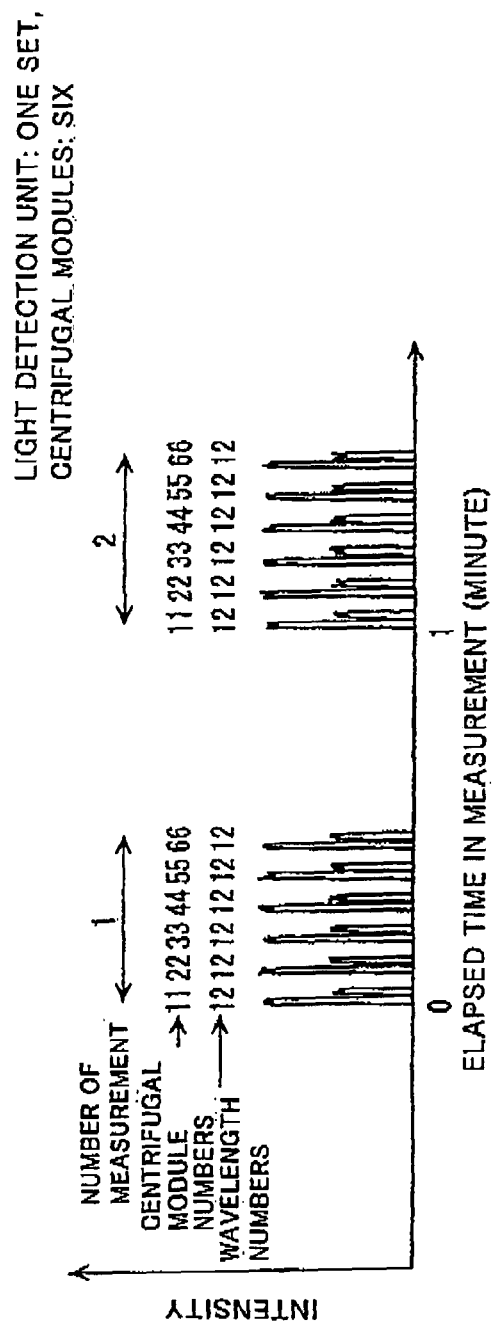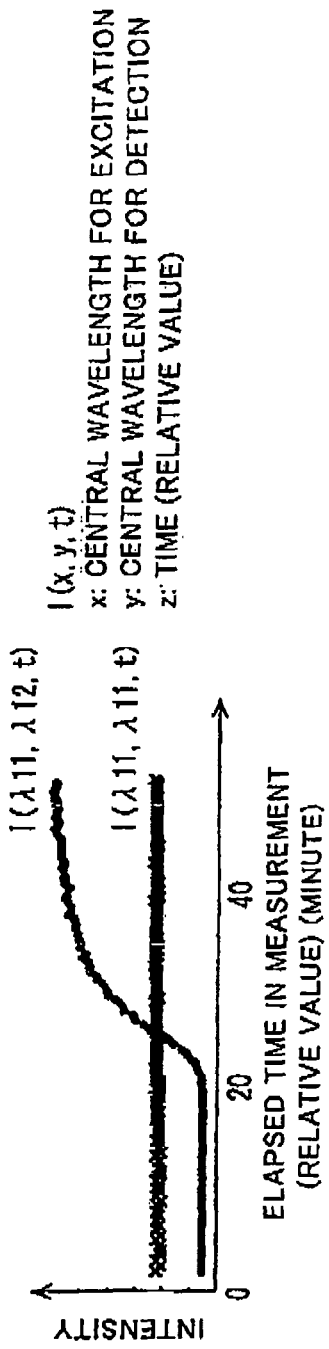

CORRESPONDING PHENOMENON

I (λ31, λ31, T):
INTENSITY OF TRANSMITTED LIGHT OF MEASUREMENT SOLUTION (WAVELENGTH = λ31)

US 7,989,163 B2

DETECTION METHOD AND DETECTION APPARATUS OF SUBSTANCE IN BIOLOGICAL SAMPLE

BACKGROUND OF THE INVENTION

The present invention relates to a method for accurately detecting fluorophore-labeled biological substances, especially, to a method for preventing erroneous results due to unexpected dusts or impurities, for example, and to a method for accurately measuring the fluorescence of a sample solution when DNA is amplified, for example, and an apparatus thereof.

Analytical techniques for DNA, protein, and the like are important in the fields of medicine and biology including gene analysis and gene diagnosis. Especially in recent years, methods and apparatuses for inspection and analysis using DNA microarrays (also referred to as DNA chips, for example), protein chips, or the like have attracted attention. The microarrays employ substrates comprising glass, for example. They are divided into a plurality (several hundreds to tens of millions) of fields, and probes for target (usually, different types of) DNA, for example, are immobilized on each field, thereby preparing each field as a minute reaction field. By causing them to react with a specimen, the target DNA in the specimen, protein, or the like is bonded to the aforementioned immobilized probes and is then captured, thereby conducting quantification. Usually, a microscope (confocal fluorescence microscope)-like apparatus referred to as a scanner is used to read fluorescence intensity emitted by the fluorescent label of the target DNA captured in each reaction field of the DNA microarrays (see Patent Document 2, for example). The apparatus irradiates an excitation light, such as a laser, onto the arrays, separates generated fluorescence from the excitation light using a dispersion element such as an interference filter, and detects fluorescence intensity via a light detector, thereby conducting quantitative and qualitative comparisons regarding captured target DNA, protein, or the like.

Regarding the detection, quantitative determination, or the like of a target nucleotide of DNA, for example, real-time fluorescence detection during amplification using a microplate, a microtube, or the like, other than the microarray is also known (see Patent Document 4).

In fluorescence measurement using the microarray, the adhesion of dust poses a great problem. Since the fluorescence intensity of a portion where dust is attached does not show an accurate value, it must be excluded from a measurement value. Usually, spots of the microarray have a size of about 100-micron diameter, and a piece of dust has a size of not more than several microns in many cases. Thus, even when a single piece of dust exists in a certain spot, by removing a signal of the portion alone, the fluorescence measurement of the spot becomes possible in accordance with the fluorescence intensity of the rest field. The spot density of microarrays has been gradually increased and the diameter of spots has become smaller. However, as the spot diameter has become smaller, the size of the spot diameter has no difference with that of dust, so that measurement via the aforementioned method becomes difficult. The same applies to a flaw in a substrate.

Patent Document 2 discloses a method for measuring the properties of a sample using fluorescence from a sample along with a reflected light of an excitation light.

A method for detecting fluorescence during amplification in a container is also performed in general. Usually, a microplate, a microtube, or the like is used as a reaction container and a detection container. Also, Patent Document 1 discloses an extraction-detection module (hereafter referred to as a centrifugal module) comprising a rotatable cartridge-like structure provided with a capturing portion for capturing DNA, virus RNA, or the like in a sample solution such as blood, and with a reagent holding portion for separately holding various types of reagents, for example. The centrifugal module feeds a sample solution via centrifugal force generated through rotation. The present module is an effective device by which it is capable of, once a sample such as blood is set, conducting all reactions and detection in the module, and the possibility of contamination to the outside is substantially low.

However, neither of the aforementioned documents discloses judgment concerning whether fluorescence from a sample is measured in a purely normal state.

Patent Document 1: WO 03/059484
Patent Document 2: JP Patent Publication (Kokai) No. 2002-310886 A
Patent Document 3: JP Patent Publication (Kokai) No. 2002-181708 A
Patent Document 4: JP Patent Publication (Kokai) No. 2002-189860 A

SUMMARY OF THE INVENTION

A detection process can be readily conducted if it is conducted in the same container as used in a reaction. In many cases, the amount of a target component (DNA, virus RNA, or the like) to be detected from a sample solution is small. After the target component is extracted from the sample solution, usually, the target component is amplified via a PCR method, an isothermal amplification method, or the like, and then is measured by detecting fluorescence. When an amplification reaction is conducted after the extraction, it is necessary to warm a reaction liquid in any methods. On this occasion, the fluorescence measurement may be provided with inaccurate results because of the reduction of the reaction liquid resulting from the evaporation of the reaction liquid, and the formation of droplets resulting from dew condensation. Also, a reagent solution is fed via centrifugal force without using a valve, so that it may be assumed that the liquid cannot be held in a predetermined position, depending on the state of the liquid or the state of the module. In this case, it is necessary to precisely judge the presence, the amount, and the state of the measurement sample solution.

It is an object of the present invention to resolve the aforementioned problem and to provide a highly accurate method for detecting a biological-related substance by which abnormality can be recognized and the results of quantification regarding a target sample are not influenced, in the case of an abnormal state where dust is attached, for example, or a sample solution is reduced or exhausted, for example.

In order to resolve the aforementioned problem, the present invention provides the following method for detecting a biological-related substance and apparatus for detecting a biological sample.

In a first aspect, the present invention provides a method for detecting a biological-related substance, in which the biological-related substance is captured in a portion for light detection and fluorescence emitted by the portion for light detection is detected, thereby performing quantitative determination regarding the target biological-related substance. The method for detecting the biological-related substance comprises labeling the biological-related substance or such a substance that is substantially the same as the biological-related substance using a fluorophore, irradiating an excitation light for exciting the fluorophore onto the portion for light detection, and detecting a light emitted by the portion for light detection after dividing the light into at least a plurality of wavelength zones. The method further comprises comparing, while one of the plurality of wavelength zones is substantially the same as that of the component of the excitation light, the light intensity of the wavelength zone that is the same as that of the excitation light component with a predetermined intensity range, and, in the case where the light intensity exceeds the intensity range, determining whether the fluorescence measurement in the portion for light detection is appropriate or not.

Further, the present invention provides a method for detecting a biological-related substance, in which the aforementioned portion for light detection comprises a region for reaction formed on a substantially planar substrate. The present invention provides a method for detecting a biological-related substance, in which light detection is continuously performed in the aforementioned portion for light detection after an amplification reaction is conducted or simultaneously during the amplification reaction. The present invention provides a method for detecting a biological-related substance, in which a biological sample is carried on any one of a DNA chip, a DNA microarray, or a protein chip. And, the present invention provides a method for detecting a biological-related substance, in which the biological sample is carried on a well of a microplate.

The present invention provides an apparatus for detecting a biological-related substance, comprising a portion for light detection disposed on a rotatable disk, a plurality of reagent holding portions for separately holding a plurality of liquids, a cartridge-like structure provided with a channel capable of shifting the liquid via centrifugal force, an optical measuring unit for detecting fluorescence emitted by the liquid and scattered light emitted by the periphery thereof, and means for judging whether the fluorescence measurement of the portion for light detection is appropriate or not on the basis of a signal from the optical measuring unit.

A target biological-related substance is measured via fluorescence detection. The fluorescence detection comprises means for irradiating an excitation light for exciting a fluorophore onto a prescribed portion for light detection of a microarray (DNA, protein), a microplate, a microtube, or a centrifugal module, and means for detecting a light emitted by the portion for light detection after dividing the light into at least a plurality of wavelength zones. In the fluorescence detection, one of the plurality of wavelength zones includes substantially the same wavelength zone as that of the component of the excitation light. The light intensity of the component of the excitation light is detected and it is compared with a predetermined intensity (threshold). The predetermined light intensity comprises a value that is set by multiplying the results of the measurement of the light intensity regarding the excitation light when a sample container and a sample solution are normal and a safe factor together. Normally, the detected light intensity does not exceed the value.

In the case where the measured intensity exceeds the threshold, the fluorescence measurement is judged to be inappropriate. In the aforementioned portion for light detection, the measurement may be conducted after the amplification reaction is performed or the aforementioned judgment may be conducted while performing the amplification reaction and real-time fluorescence detection. Various methods can be applied to the amplification reaction. Preferably, an isothermal method is used for easiness of operation.

As another embodiment of the present invention, an apparatus for analyzing a biological sample comprises a rotatable disk capable of controlling the rotation thereof, a portion for light detection disposed on the rotatable disk, a reagent holding portion for holding a sample disposed on the rotatable disk, a channel capable of shifting the sample disposed on the rotatable disk to the portion for light detection via centrifugal force, an optical measuring unit for detecting a light emitted by the portion for light detection, and a display apparatus for displaying the state of the sample in the portion for light detection on the basis of a signal from the optical measuring unit.

In the case where dewdrops are generated in the portion for light detection, the display apparatus is capable of displaying the fact that the measurement state of the sample is in an abnormal state. Also, in the case where the sample is reduced to less than a predetermined value in the portion for light detection, the display apparatus is capable of displaying the fact that the measurement state of the sample is in the abnormal state. Moreover, in the case where the sample is unevenly positioned in the portion for light detection, the display apparatus is capable of displaying the fact that the measurement state of the sample is in the abnormal state.

BRIEF DESCRIPTION OF THE DRAWINGS

FIG. 3 shows a control block diagram of the analytical apparatus of FIGS. 2A and 2B.

FIGS. 9A-9K show a flow diagram illustrating a shift process of reagent solution, for example, using the centrifugal module of embodiment 1.

DESCRIPTION OF THE PREFERRED EMBODIMENTS

In the following, embodiments of the present invention are described.

Embodiment 1

Figure 1A:
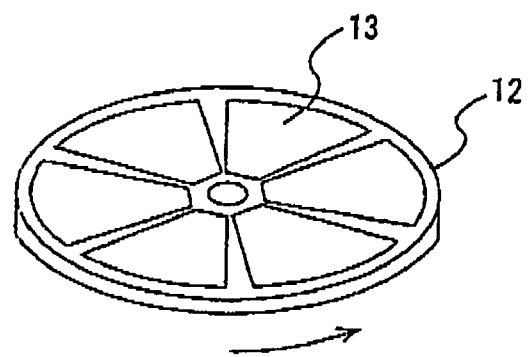
FIG. 1A shows a perspective view of the structure of a centrifugal disk of an analytical apparatus used in the present invention.
Figure 1B:
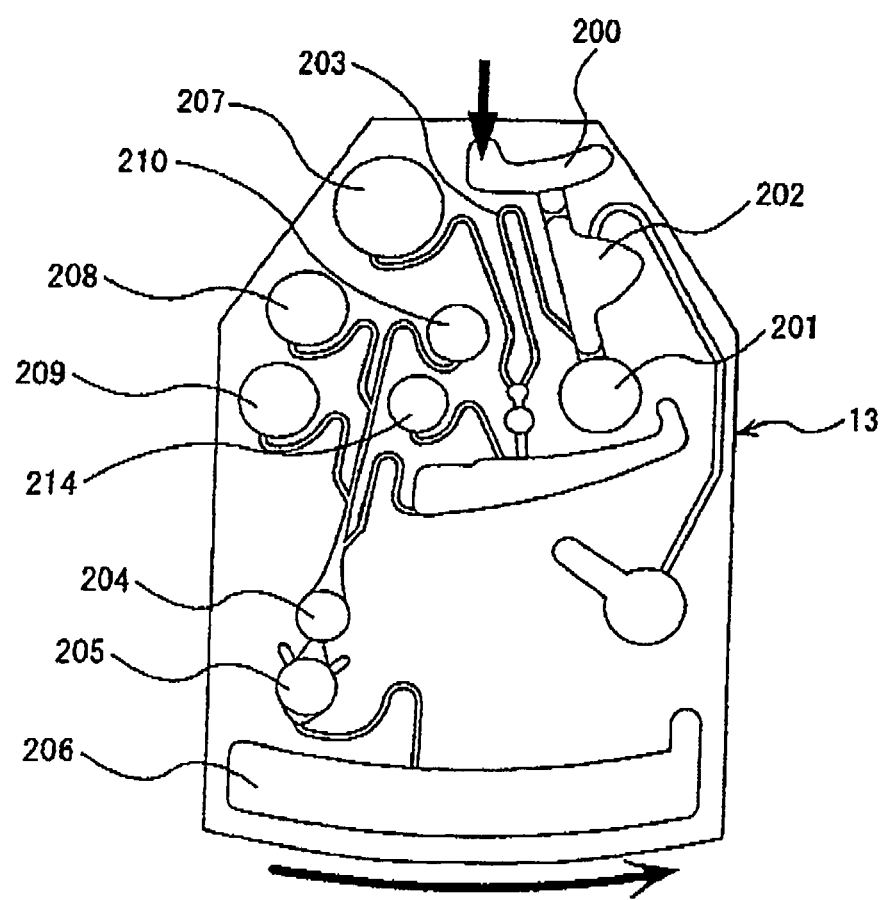
FIG. 1B shows a plan view of the structure of the centrifugal module disposed in the disk of FIG. 1A.

First, the operation of a centrifugal module used in the present invention is described. FIGS. 1A and 1B show the configuration of important elements of a chemical analyzing module using centrifugation employed in the present invention. FIG. 1B shows a segment having a prescribed configuration of a passage for analysis or one of centrifugal modules 13. In an actual analysis, a plurality of the segments 13 shown in FIG. 1B, namely, four to twelve segments, for example, are fittingly mounted on a holder disk 12 shown in FIG. 1A. The centrifugal module 13 is made of PMMA (polymethyl methacrylate), for example. The centrifugal module 13 may be disposable so that it can be discarded after a single use.

In FIG. 1B, various types of reagents are held in minim containers 207, 208, 209, 210, and 211, and the surfaces thereof are sealed with a plastic film. An operator dispenses whole blood to a whole-blood container 200 and rotates the disk, whereby the whole blood is shifted to the outer circumference via centrifugal force and is then separated into a cellular component 201 and a plasma component 202 in accordance with the difference in density.

A narrow passage (capillary) 203 is bifurcated from the container 202 for holding the plasma component, and the passage has a structure where it is once returned to the inner circumference. Thus, the plasma cannot go through the capillary.

When the rotation is stopped, the narrow passage 203 is completely filled with the plasma via capillary flow force. By rotating the disk again, the plasma drains from the narrow passage. The outlet of the narrow passage is positioned outer than the inlet (bifurcation from a plasma container) in terms of the circumference, so that all the plasma in the narrow passage drains on the siphon's principle. In this occasion, when a ventilation hole is provided on the film by which the first reagent container 207 is sealed, the reagent drains from the container 207 and is mixed with the plasma. Preferably, the ventilation hole is provided at a desired time for reagent supply immediately before the rotation of the disk.

After the first reagent and the plasma are sufficiently mixed, the rotation of the disk is stopped and a hole is provided on the film of a second reagent container 214. By rotating the disk again, the reagent flows to a reaction container, forces out the liquid in the reaction container, and then flows into a recovery container 205 through a capturing filter 204. The capturing filter 204 comprises fibrous glass and nucleic acid is adsorbed on the glass surface. Further, third and fourth reagents are caused to flow from the containers 208 and 209, and the nucleic acid adhered to the fibrous glass is washed. The liquid that has passed through the capturing filter 204 flows into the recovery container 205 and drains on the siphon's principle from the recovery container. The eluent including nucleic acid is held in the recovery container 205. The used reagent and the cleaning liquid, for example, are transmitted to a waste container 206 from the recovery container.

Figure 2:
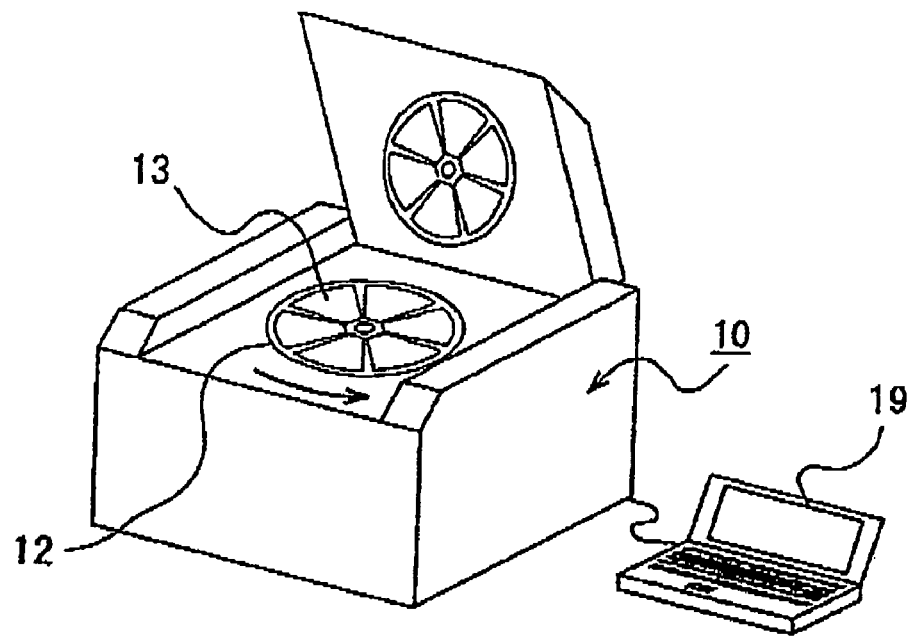
FIG. 2A shows an outline perspective view of an analytical apparatus using a method for detecting a biological-related substance in embodiment 1.
FIG. 2B shows a sectional side view of the analytical apparatus of FIG. 2A.
Figure 2B:
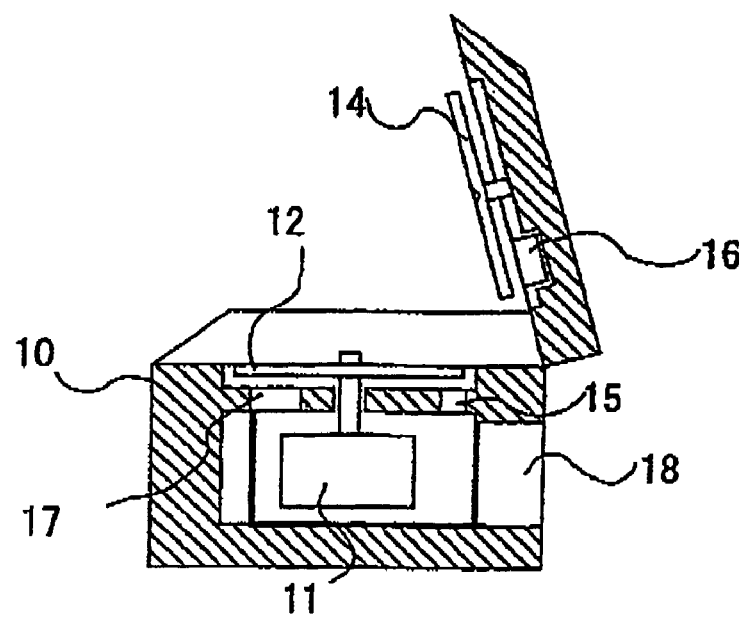

FIG. 2A shows a general view of an analytical apparatus using the method for detecting a biological-related substance according to the present invention. FIG. 2A shows an appearance perspective view, FIG. 2B shows a cross-sectional view of a portion thereof, and FIG. 3 shows a control block diagram thereof. An analytical apparatus 10 comprises a centrifugal motor 11, a holder disk 12 rotatably supported via the motor 11, and a centrifugal module 13 positioned and held in the holder disk 12, the centrifugal module 13 being capable of conducting extraction or reaction in the inside thereof through the rotation of the motor 11. Also, the analytical apparatus 10 comprises a disk presser cap 14 for stably holding the centrifugal module 13 during rotation, a detector 15 for determining the disk position so as to accurately control the position of the centrifugal module 13, namely, the rotation position of the holder disk 12, and a punching unit 16 in which a punching pin for controlling the feed of a liquid in the centrifugal module 13 is disposed. Further, the analytical apparatus 10 comprises an optical detection light irradiating and receiving portion 17 for detecting light, an optical detection unit 18, and a controller PC 19 for conducting an analysis display of data, for example. Although a marker for positioning in the holder disk, a temperature regulation unit, such as a heater, for controlling the temperature of the holder disk 12, a control circuit, a power circuit, and the like are necessary, they are omitted in FIGS. 2A and 2B.

In accordance with the control blocks shown in FIG. 3, the apparatus of FIGS. 2A and 2B are controlled. First, an analysis is initiated by inputting measurement conditions to a controller PC 301, and various controls are performed via a control CPU 302 in the analytical apparatus 10. Control units include a motor control unit 303, a light detection control unit 306, a punching control unit 305, and a temperature control unit 304. The motor control unit 303 controls a motor, a rotation frequency sensor, a positioning sensor, and a malfunction detection sensor (for motor temperature, abnormal rotation frequency, or the like). Also, the motor control unit 303 rotates the motor on the basis of a specified rotation frequency and acceleration or deceleration time under the directions from the CPU 302, and it shifts a liquid in the centrifugal module 13 via centrifugal force.

The punching control unit 305 controls a motor for extruding a plurality of the punching pins contained in the punching unit 16. By extruding a pin at a specified location, a hole is provided on the plastic film of the specified reagent container in the centrifugal module 13, and the reagent can be shifted via centrifugal force. Before this operation, it is necessary to position the holder disk 12 and the centrifugal module 13 via the motor control unit, and then the operation is performed after the positioning.

The temperature control unit 304 adjusts the temperature of the centrifugal module 13 or the holder disk 12. Also the temperature control unit 304 controls, using a known method, a heater 4 and a temperature sensor (not shown in the drawings) closely-attached to the centrifugal module, and a heater-cooler and a temperature sensor disposed in a chamber where the holder disk 12 is contained. The light detection control unit controls a light source, a light detector, a motor for switching filters, a filter identification sensor, a shutter for optical stopping, and a data transfer unit of the malfunction detection sensor (when a lamp at the light source is burned out, for example), thereby measuring the light intensity of an emitted light.

Figure 4:
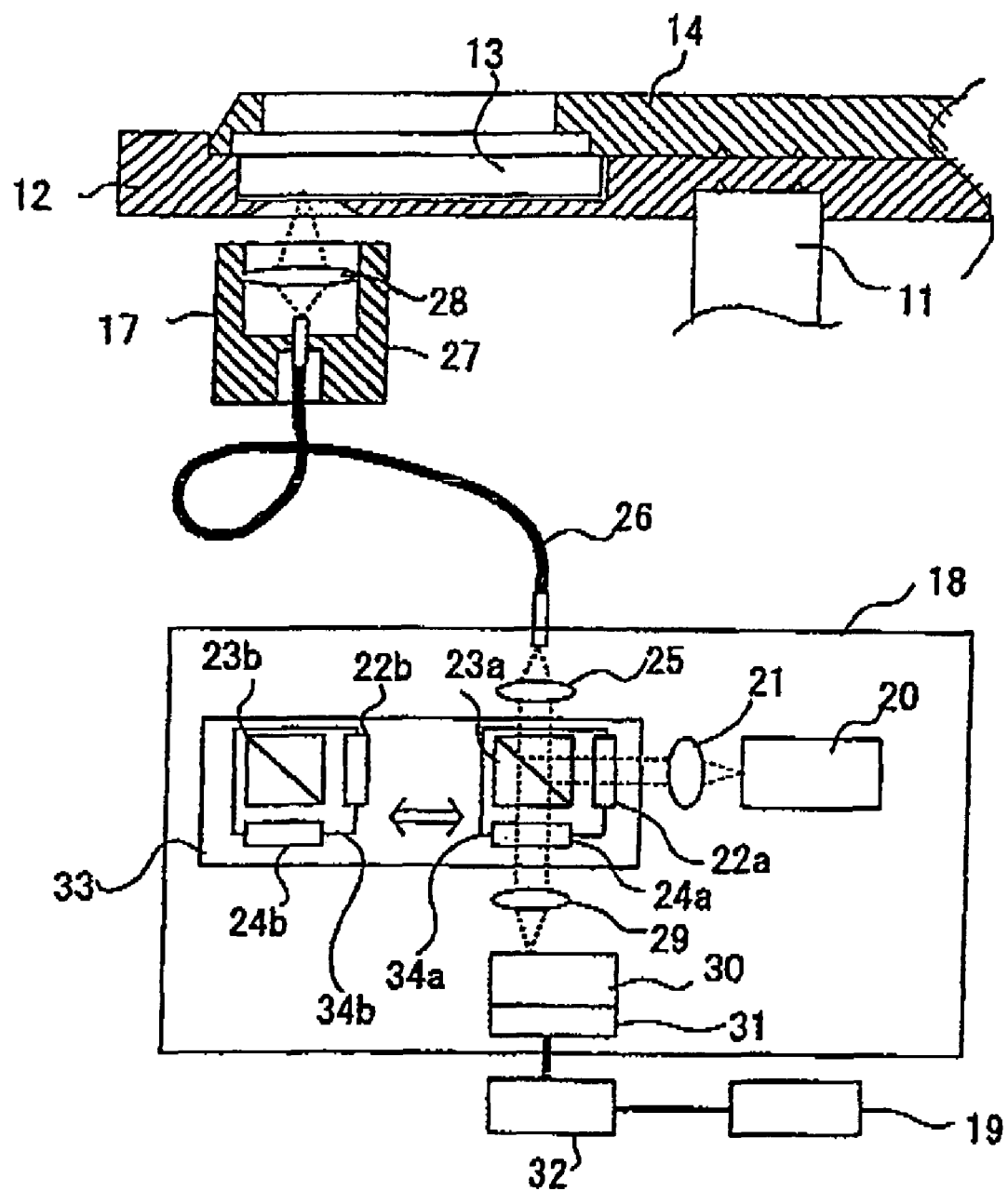
FIG. 4 schematically shows an example of an optical detection system with a sectional view of a portion thereof.
Figure 5:
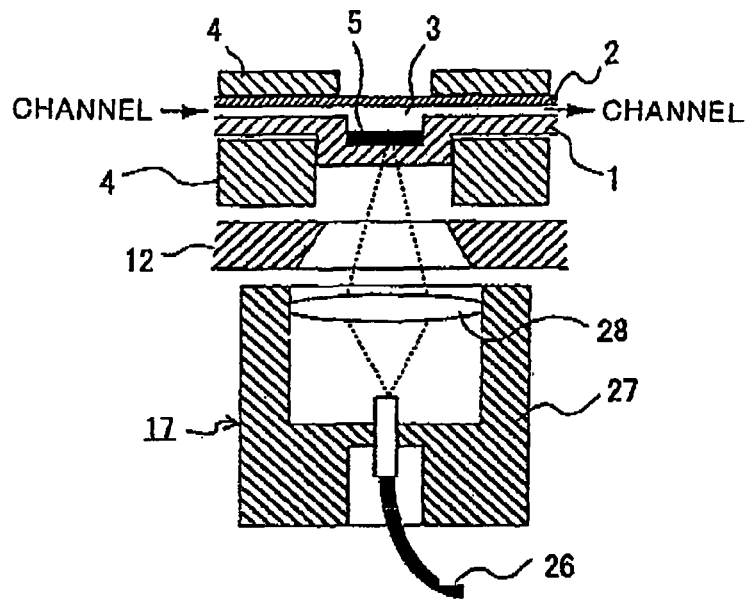
FIG. 5 shows an enlarged view of a state where a light is irradiated onto the centrifugal module of embodiment 1.

FIG. 4 shows a general configuration of an optical detection portion and FIG. 5 shows an enlarged view of a light irradiation portion for the centrifugal module. FIG. 4 shows a portion for light detection 3 (extraction/detection port) of the centrifugal module, the optical detection light irradiating and receiving portion 17, and the optical detection unit 18 (see Patent Document 1 for the centrifugal module). In FIG. 5, the portion for light detection 3 (extraction/detection port) of the centrifugal module 13 is comprised of a concave-shaped transparent material in the lower portion and is covered with a transparent film 2 in the upper portion. The portion for light detection 3 forms a space of suitable volume and constitutes a cell structure for light measurement. A measurement sample solution 5 is held in the space and light is detected. In the measurement sample solution 5, extracted RNA and a reagent for amplification detection are mixed, for example.

Regarding the reagent for amplification, a known NASBA kit is used. Concerning a probe for detection, the probe is oligonucleotide and bounded a fluorophore reporter and quencher, as well known, and the probe generates fluorescence emission by irradiation of excitation light when the probe is hybridized. In this state, a reaction liquid is adjusted to be 41° C. via an external heater 4 and fluorescence measurement is conducted. The measurement can be conducted by other amplification methods in the same manner. In those cases, reagent varieties and setting values, such as temperatures, depends on each amplification method.

The optical detection light irradiating and receiving portion 17 is disposed in the vicinity of the centrifugal module, performing light irradiation onto the centrifugal module and reception of fluorescence, for example. The optical detection unit 18 includes other light source, spectroscopy, light detection, and the like, performing the measurement of a target light intensity. Both units are connected via an optical fiber. A light from an excitation light source 20, such as a laser light source or a mercury lamp, is introduced into an optical fiber 26 (NA=0.22, core diameter: 400 μm) through a lens 21, a monochromatization filter 22 for excitation lighting, a dichroic mirror block 23, and an objective lens 25. Other end of the optical fiber 26 is disposed in the optical detection light irradiating and receiving portion 17 and the light is condensed in the portion for light detection 3 (extraction/detection port) via a lens 28. The lens 28 and the optical fiber 26 are disposed in a holder 27 such that their positions are adjustable. The entire holder has an XYZ-adjust function, so that the holder can accurately perform light irradiation onto the portion for light detection 3 (extraction/detection port).

Fluorescence (including scattered light, reflected light, and the like) emitted by the measurement sample solution 5 in the portion for light detection 3 (extraction/detection port) is collected via the lens 28 and is introduced into the optical detection unit 18 through the optical fiber 26.

The fluorescence, for example, is collimated again via the objective lens 25 and a necessary light component is selected via the dichroic mirror block 23 and an optical cut filter 24 for fluorescence detection. The light component is condensed via the lens 29 and detected via a detector. In this case, a spectroscope 30 and a CCD line sensor 31 are employed as the detector. The intensity of light divided by wavelength is measured and data thereof is transmitted to the controller PC 19 through a control unit 32, and the data is processed.

Figure 6:
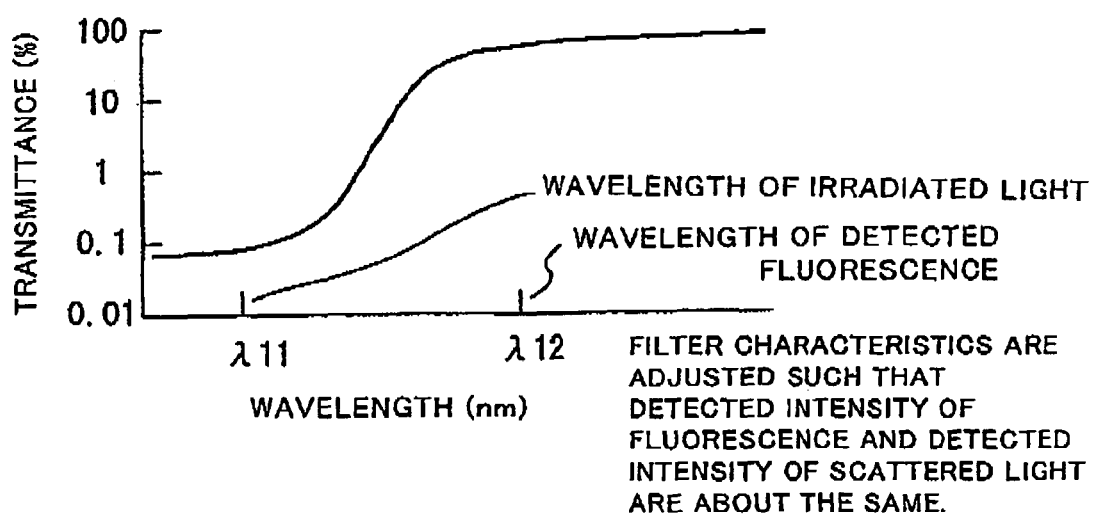
FIG. 6 shows a graph of the characteristics of a cut filter for fluorescence measurement in embodiment 1.

FIG. 6 shows an example of the optical cut filter for fluorescence detection. In fluorescence measurement, the optical cut filter for fluorescence detection usually employs a filter of such characteristics that do not allow excitation light to transmit as much as possible (the transmittance of an excitation wavelength is not more than 0.0001% and the transmittance of a fluorescence wavelength zone is not less than 80%, for example), in general. In FIGS. 4 and 5, the components of the excitation wavelength and fluorescence wavelength are simultaneously transformed into spectra and detected via the line sensor. Thus, as shown in FIG. 6, the filter has characteristics by which the transmittance of the excitation wavelength zone is about 0.1% and the transmittance of the fluorescence wavelength zone is not less than 80%, such that the components of the excitation wavelength are partially transmitted. Generally, the fluorescence intensity of a fluorophore is very weak (because of a low concentration of the fluorophore, namely, about 1 nM) and the scattered light intensity is sufficiently large as compared with the fluorescence intensity. Thus, the intensity ratio is large, so that they cannot be measured as they are using the same detector. Also, with a conventional filter, the components of the scattered light are cut, so that the scattered light intensity cannot be monitored. Therefore, it is desirable to use a filter as in FIG. 6 and to set the intensity of fluorescence that is to be observed and the intensity of standard scattered light such that they have almost the same intensity level.

Figure 7:
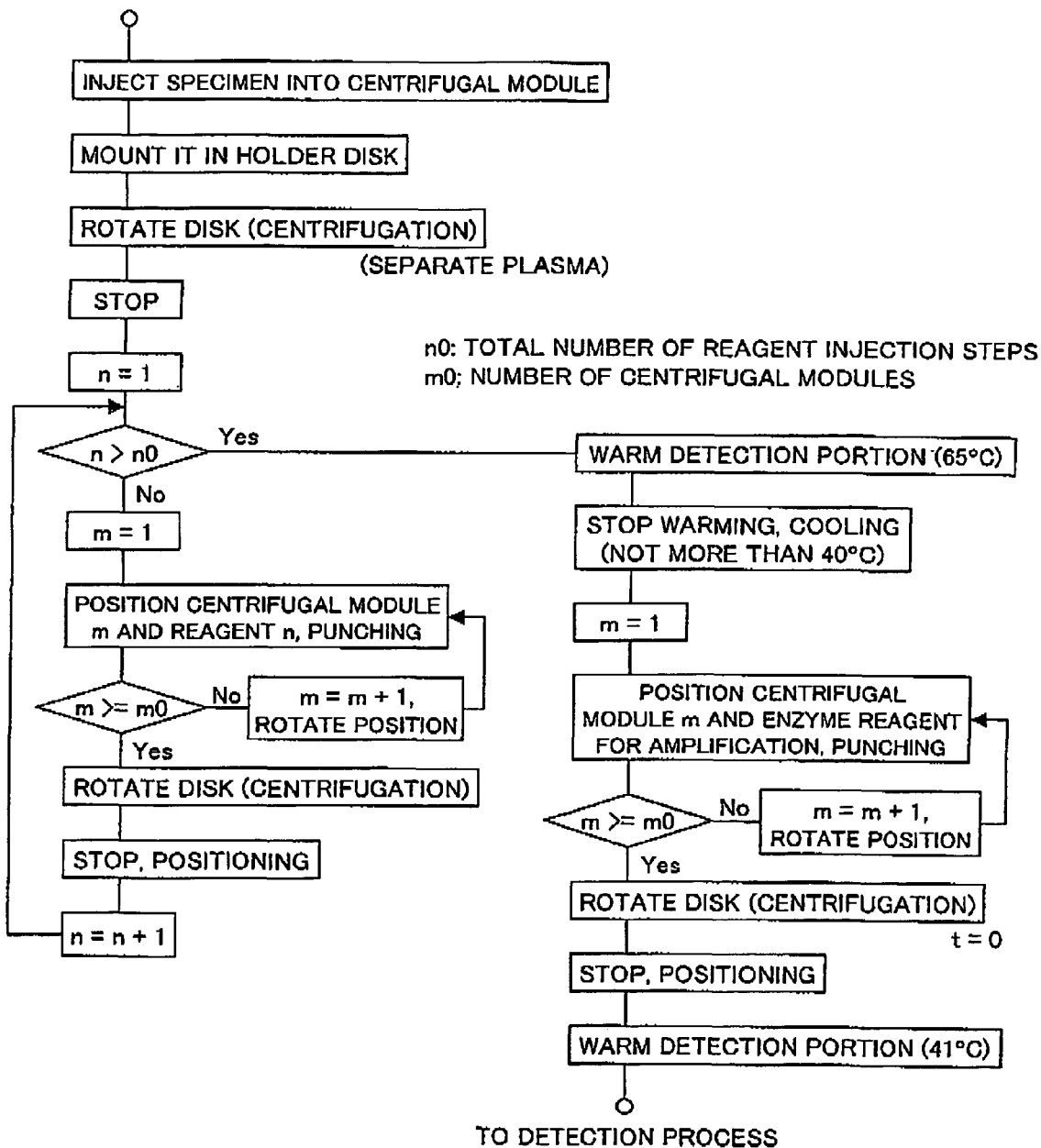
FIG. 7 shows an operating procedure of analysis regarding the analytical apparatus of embodiment 1.

FIG. 7 shows a flow diagram of an operating procedure regarding the analytical apparatus. Basically, the procedure is conducted in the same manner as Patent Document 1. First, a specimen is injected into a predetermined position of the centrifugal module and the module is mounted in the holder disk. The disk is rotated and stopped on the basis of a predetermined rotation speed and a rotation time to separate plasma component. Then, necessary reagent (including cleaning liquid) is introduced individually in a predetermined order, thereby extracting a target component, such as virus RNA. In order to introduce a first reagent into a first module, the position of the first module is adjusted through the rotation via a motor, and a sealing film is punched at the position of the first reagent. This process is conducted as many times as the number of modules.

Thereafter, the disk is rotated and stopped on the basis of the predetermined rotation speed and the rotation time, so that the first reagent is shifted and then mixed. By conducting this operation as many times as the number of necessary reagent, a target component is extracted in the portion for light detection (extraction/detection port). Then, a reagent 1 for amplification (such as primer) is injected and mixed in the same operation, and an amplification detection process is conducted. First, the portion for light detection (extraction/detection port) is warmed to 65° C., and then it is cooled to not more than 40° C. The positioning and punching of a sealing film at a storage portion of reagent for amplification (such as enzyme solution) are conducted as many times as the number of modules. The disk is rotated and stopped on the basis of the predetermined rotation speed and the rotation time, so that the enzyme solution, for example, is mixed. The module is warmed to 41° C. and is maintained, thereby causing an amplification reaction. The state of the amplification is measured in a fluorescence detection process.

Figure 8:
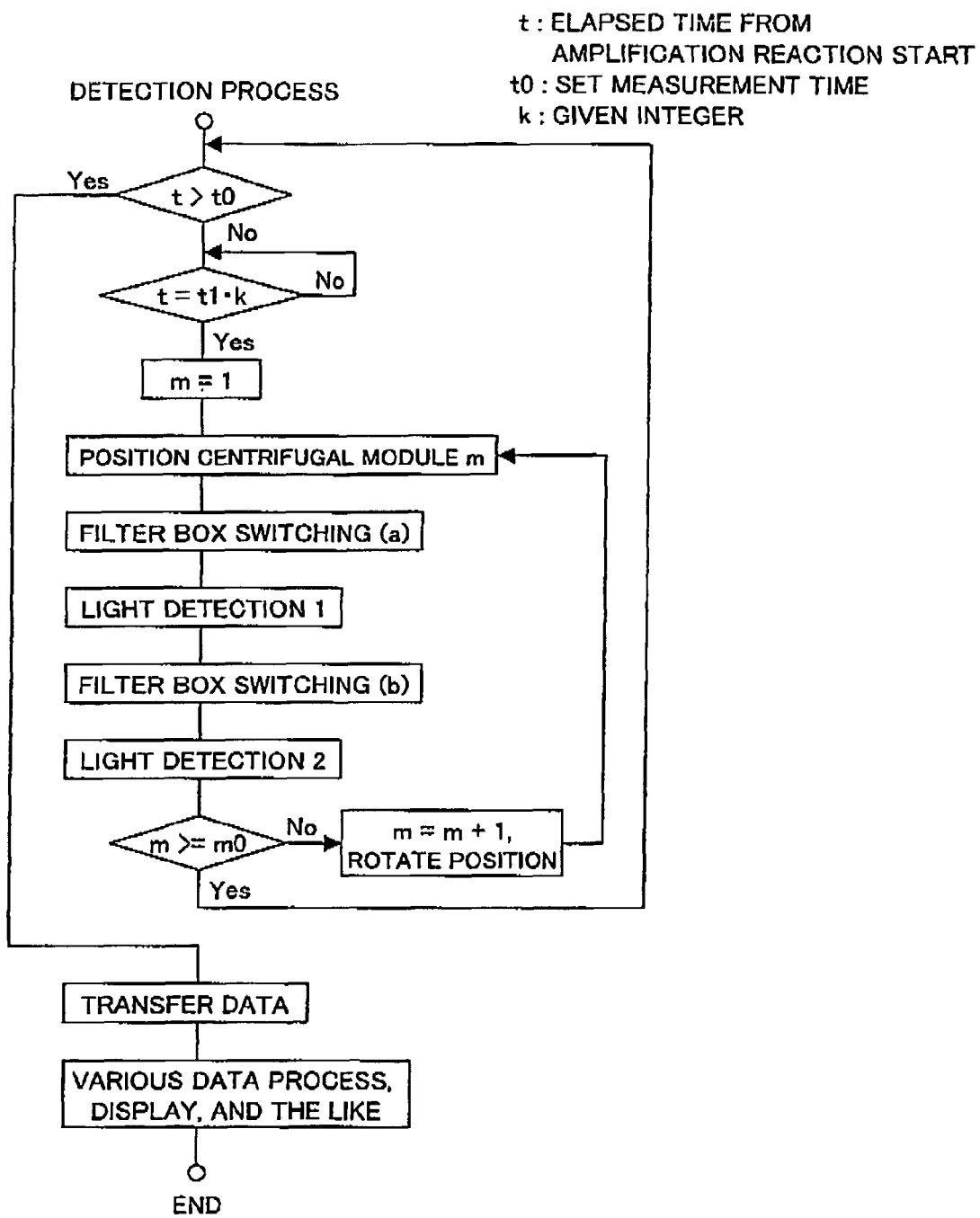
FIG. 8 shows an operating procedure of a fluorescence detection process in embodiment 1.

FIG. 8 shows a flow diagram of a detection process procedure regarding the analytical apparatus. By measuring at specified light measurement time intervals t1 in a repeated manner, elapsed time is measured. A total of measurement time is represented by t0. Usually, to is set from about 60 minutes to 90 minutes, and t1 is set about 0.5 minute. The first module is positioned and fluorescence is measured. The present example shows a case where two types of fluorophores (such as FAM® and ROX®) are assumed as fluorescence detection objects and each has two types of excitation wavelengths (such as 480 nm and 590 nm). BOX-A34$a$ and BOX-34$b$ are switched via a filter box switch 33.

The BOX-A34$a$ and BOX-B34$b$ each comprises monochromatization filters 22$a$ and 22$b$ for excitation lighting, dichroic mirror blocks 23$a$ and 23$b$, and cut filters 24$a$ and 24$b$ for fluorescence measurement, so that it is possible to measure fluorescence at different wavelengths. Thus, light detection is conducted by switching to the BOX-A34$a$ using the filter box switch 33, and then light detection is conducted by switching to the BOX-B34$b$. This process is conducted as many times as the number of modules. This operation is repeated for a time of t0 at intervals of t1.

FIGS. 9A-9K show a diagram illustrating a transferred state of reagent solution using one centrifugal module shown in FIG. 1B. A liquid shift and a reaction state in an amplification process are described. The diagram shows only a descriptive portion and other portions are omitted. In the portion for light detection (extraction/detection port), a target component is extracted in the extraction process. In reagent A and reagent B ports, reagent for detecting an amplification reaction is encapsulated, respectively (FIG. 9A). A sealing film of the reagent A is punched via the punching unit (FIG. 9B). The reagent in the reagent A is shifted to the portion for light detection (extraction/detection port), and then mixed via centrifugal force through rotation (FIG. 9D). The portion for light detection (extraction/detection port) is warmed to 65° C., maintained for five minutes, and then cooled to not more than 40° C.

The sealing film of the reagent B is punched via the punching unit. The reagent in the reagent B is shifted to the portion for light detection (extraction/detection port), and then mixed via centrifugal force through rotation (FIG. 9I). The module is warmed to 41° C. and is maintained, thereby causing an amplification reaction.

FIGS. 10A-10G show examples of light detection results obtained by the above operations. An oligonucleotide with a fluorophore reporter including FAM is used. The monochromatization filter for excitation light employs a filter that passes from 470 to 490 nm, and the cut filter for fluorescence measurement employs a custom-made filter (substitutable with a GG 495 colored glass filter). A CCD-line sensor 31 is capable of detecting light from 350 to 700 nm. However, in the present embodiment, the intensity of the 470 to 490 nm band (wavelength component of excitation light) and the intensity of the 530 to 540 nm band (wavelength component of fluorescence regarding the fluorophore) are detected as data.

Figure 10:
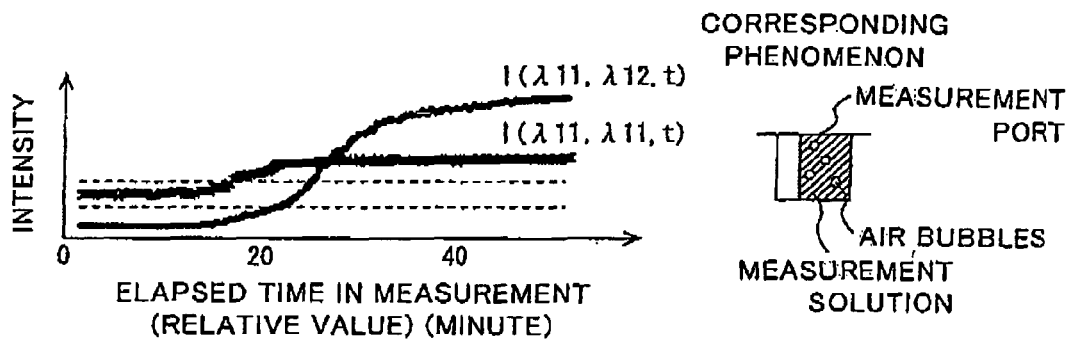
FIGS. 10A-10B show graphs of an example of a light detection result in a normal case in embodiment 1.
FIGS. 10C-10E show graphs of an example of a light detection result in the case where a measured value is abnormal in embodiment 1.
FIGS. 10F-10G show graphs of another example of a light detection result in the case where a measured value is abnormal in embodiment 1.
Figure 10:
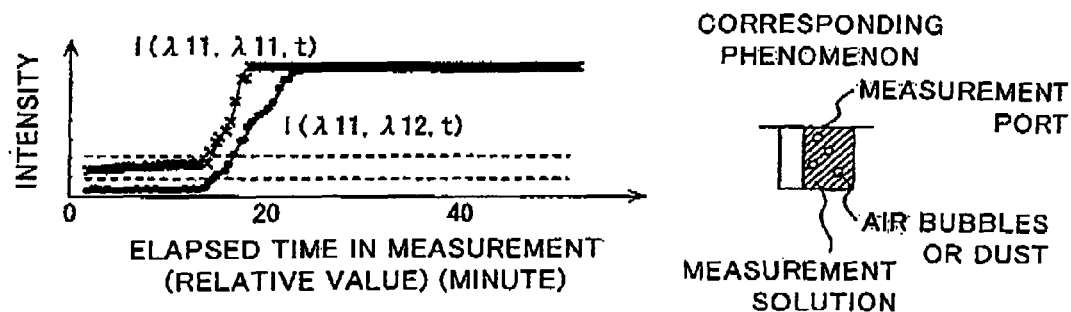
Figure 10:
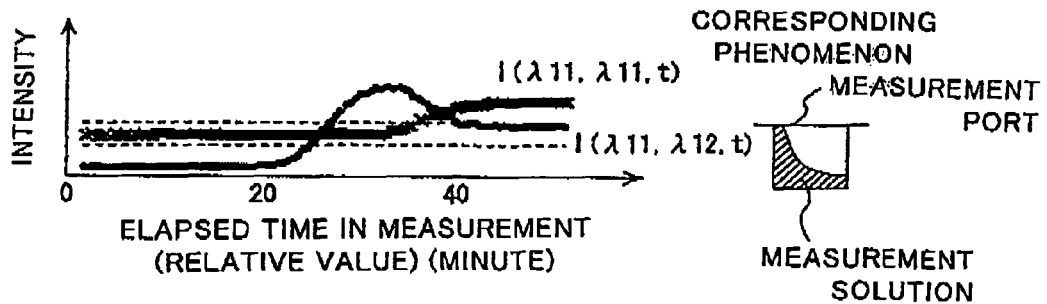
Figure 10:
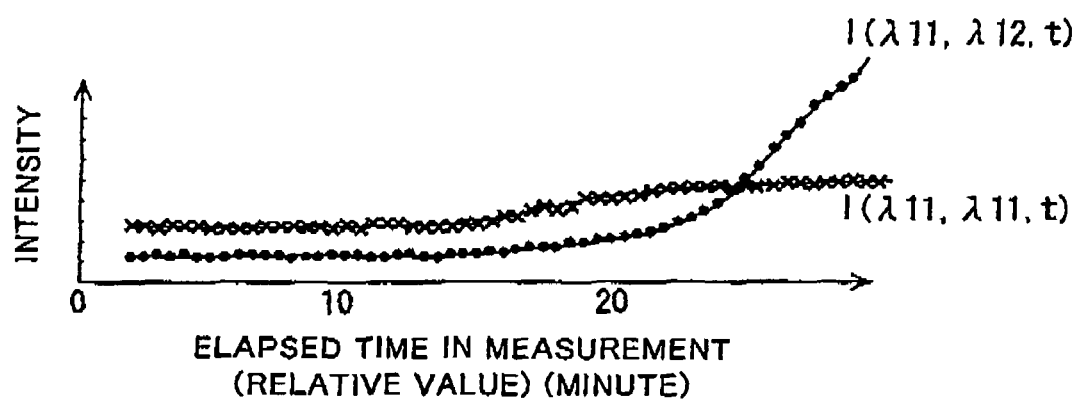
Figure 10:
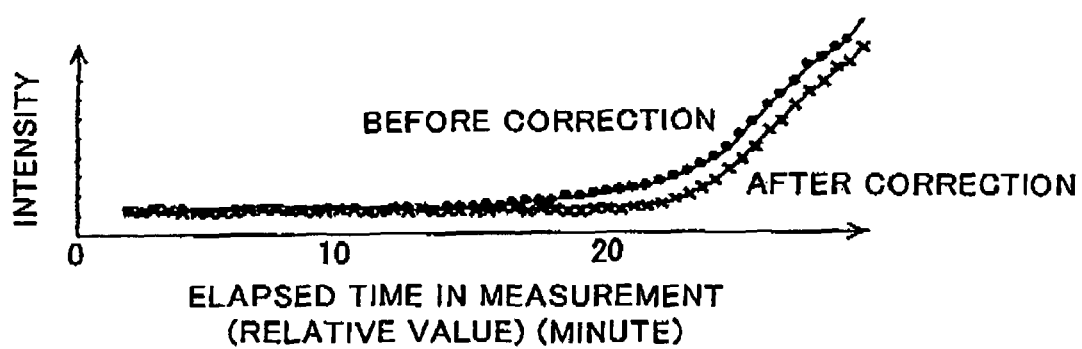

FIG. 10A shows a diagram of a measurement result regarding a signal intensity gained by every 0.5 minute after the module is maintained at 41° C. The intensity of detected signal is obtained in order of elapsed time (centrifugal module No., detected wavelength, elapsed time (number of every 0.5 minute))=(1,1,0), (1,2,0), (2,1,0), (2,2,0) . . . (5,1,1), (5,2,1), (6,1,1), (6,2,1) . . . .

FIG. 10B shows only those signals extracted from a given centrifugal module, indicating time change. I ($\lambda$11, $\lambda$12, t) shows a component of a fluorescence wavelength, and I ($\lambda$11, $\lambda$11, t) shows the intensity of a component of an excitation light wavelength. FIG. 10B shows a change in a normally measured case, in which an amplification reaction is caused with the passage of time, and fluorescence is increased. In this case, the intensity of the component of the excitation light wavelength is almost unchanged, and the intensity does not exceed a threshold value. By measuring the intensity of the component of the excitation light wavelength about ten times in a normal state, the threshold value is set as an average thereof plus or minus 6σ. The value is variable depending on a measurement system, so that it is necessary to predetermine the value when conditions are changed.

FIGS. 10C, 10D, and 10E show the passage of time regarding a light detection result in the case where measured values are abnormal. FIG. 10C corresponds to the result of a case where a sample solution is warmed, so that a phenomenon as shown to the right of FIG. 10C takes place, thereby generating air bubbles in the inside or at the inner walls of a container or thereby allowing dust as scatters to mix thereinto. The component of the fluorescence wavelength does not indicate a significant change. However, FIG. 10C shows a state where the intensity of the component of the excitation light wavelength is fluctuating, and exceeds the threshold value. FIG. 10D shows a case where the scatters, such as air bubbles, are extremely increased, and the component of the fluorescence wavelength changes abnormally. FIG. 10E shows another example of the abnormal case. As shown to the right of FIG. 10E, FIG. 10E is an example of change where the localization state of the measurement solution in the portion for light detection (extraction/detection port) is changed.

In this manner, the formation of the scatters in the measurement solution can be detected using the intensities of the component of the excitation light wavelength. All the intensities are the same in terms of reactions, and the results are originally the same. However, when only a component of a wavelength of a target fluorophore is measured, the result may show a different intensity, namely, a different nucleic acid concentration as shown by I ($\lambda$11, $\lambda$12, t) of FIGS. 10C, 10D, and 10E. By simultaneously monitoring the intensity of the component of the excitation light wavelength, the abnormality of the reaction liquid can be detected, and erroneous results can be prevented, thereby improving detection accuracy.

In the case where a droplet is formed, the reaction liquid volume is reduced, so that the concentration of a reaction reagent is caused to rise. This may become an impediment to the amplification reaction. In the present example, such an abnormality can also be detected. Moreover, in the case where the centrifugal device has failure, such as a warp, a flaw, or the like, abnormality can be detected in the same manner, since the intensity of the component of the excitation light wavelength is increased due to the flaw.

Although one type of probe is used in the present example, the present example can also be realized in the same manner using a plurality of types of probes. Particularly, in the case of one type of excitation wavelength and a plurality of target fluorophores, the present example can be realized exactly in the same constitution. FIG. 10F shows another example of an abnormal case. Scattered light intensity I ($\lambda$11, $\lambda$11, t) is fluctuating as shown in the figure and influences fluorescence intensity I ($\lambda$11, $\lambda$12, t). As the I ($\lambda$11, $\lambda$11, t) increases, the I ($\lambda$11, $\lambda$12, t) also increases. Since the effects of the I ($\lambda$11, $\lambda$11, t) on the I ($\lambda$11, $\lambda$12, t) are almost constant, by correcting effects of the I ($\lambda$11, $\lambda$11, t), only the fluorescence intensity without the effects of the I ($\lambda$11, $\lambda$11, t) can be calculated as shown in FIG. 10G, thereby enabling accurate measurement.

Figure 21:
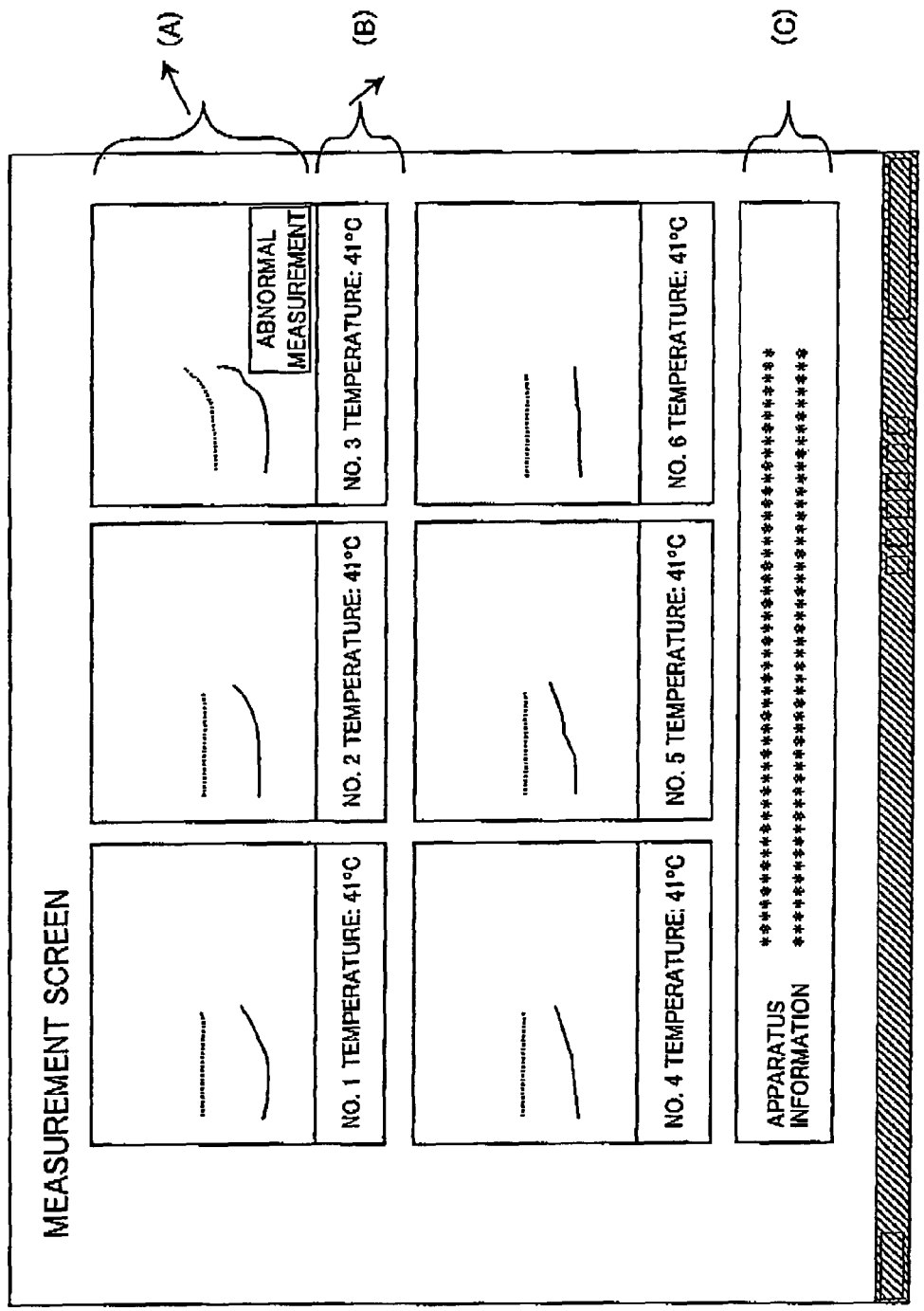
FIG. 21 shows an example of a display screen for measurement in embodiment 1.

FIG. 21 schematically shows a measurement screen of the controller PC 19 during measurement. FIG. 21 shows an example of a measurement where six centrifugal modules are set. A display window is allotted to each centrifugal module, and the time waveforms (the same waveforms as those in FIGS. 10B, 10C, 10D, 10E and 10F) of a result of light detection regarding the change of fluorescence intensity, a measurement result of a temperature control state in each centrifugal module, and the like, are displayed in an (A) field in real time (the types of displayed waveforms can be selected by a user).

In the lower portion (B) of individual display windows, an individual information display window is disposed, in which a module number, controlled temperature, actual temperature, and the like are displayed. Also, regarding a state of the entire apparatus, information about elapsed time, sample information, the number of rotation, the number of steps, and the like are displayed in a separate window. Concerning display data in the display window, history of the transition of temperature in the module (control result), for example, can be selected and displayed, in addition to the case of the result of fluorescence intensity as shown in the figure. In the case of the results as in FIGS. 10C to 10E, alert messages that indicate an abnormal state, such as "Abnormal measurement", "Abnormal state!!" or the like, are displayed on the display window of a corresponding module. Also, a function is provided by which, when all modules are abnormal, a message window asking whether to abort or continue the measurement is displayed so as to allow a user to select. In the case of FIG. 10F, a message box asking "Scattered intensity increased; correct?" is caused to blink in order to urge a user's judgment. Information about the entire apparatus is also displayed in a (C) field.

When a result is printed with a printer in addition to the screen display, the comment "Abnormal state!!" for example, is added to the line of a corresponding sample in a measurement list and an output is performed. In the case of FIG. 10F, the comment "Corrected" is attached and the result on the basis of the corrected intensity is outputted.

Embodiment 2

Figure 11:
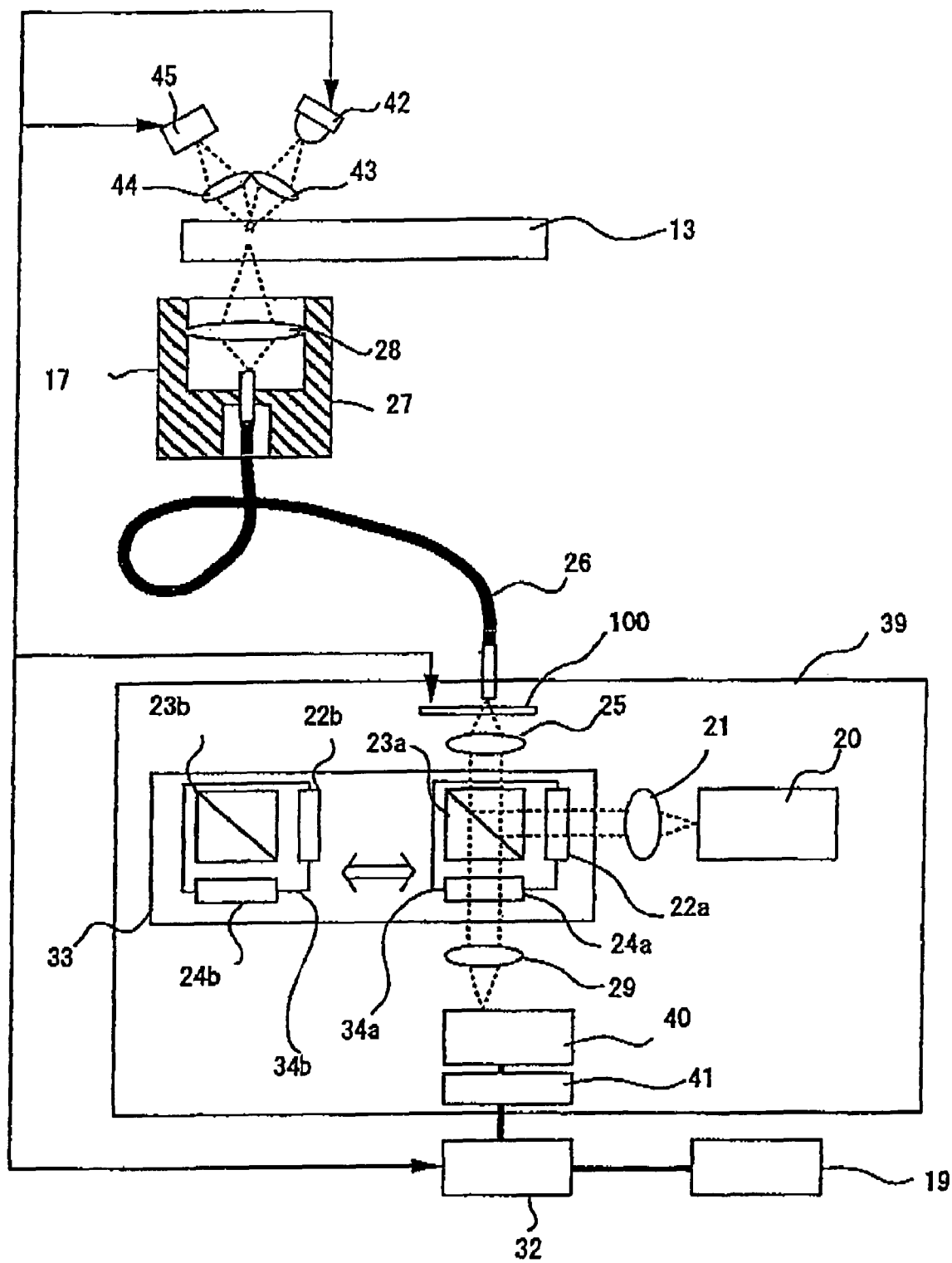
FIG. 11 shows a configuration diagram of an optical detection portion of embodiment 2.

FIG. 11 shows a configuration diagram of another optical detection portion 39 of the analytical apparatus using the method for detecting a biological-related substance. The method for detecting fluorescence is basically the same as in FIG. 4. The light intensity is detected using a photomultiplier 40 as a light detector instead of the spectroscope and the line sensor. A signal of the photomultiplier is amplified and converted from analog to digital via an analog-to-digital converter 41, and then the signal is transmitted to a control unit 32. Since fluorescence is transformed into spectra using cut filters 24a and 24b for fluorescence measurement, the filters have characteristics for normal fluorescence detection such that excitation light is not allowed to transmit to a maximum extent. The detection of scattered light as shown in embodiment 1 is conducted via another optical system. As shown in the figure, a light emitting diode (LED) 42 is disposed as a light source above the centrifugal module, and a light thereof is condensed via a lens 43, while scattered light, for example, is condensed via a lens 44 and detected via a photodiode 45, and then they are transmitted to the control unit 32.

It is not necessary to strictly position a scattered light monitor, so that a measurement field can be covered widely by directly detecting from above, thereby detecting abnormality in a wide area. Also, it is not necessary to use the same wavelength as that of an excitation light, so that a measurable wavelength can be readily set. Moreover, as a spectroscopic process is unnecessary, adjustment can be easily conducted, so that a construction can be readily conducted as above. By employing a structure by which scattered light measurement and the light detection of a target component are conducted via separate optical systems, the optical detection portion can be diverted to the measurement of chemiluminescence, for example, in addition to fluorescence, thereby widening application.

Figure 12:
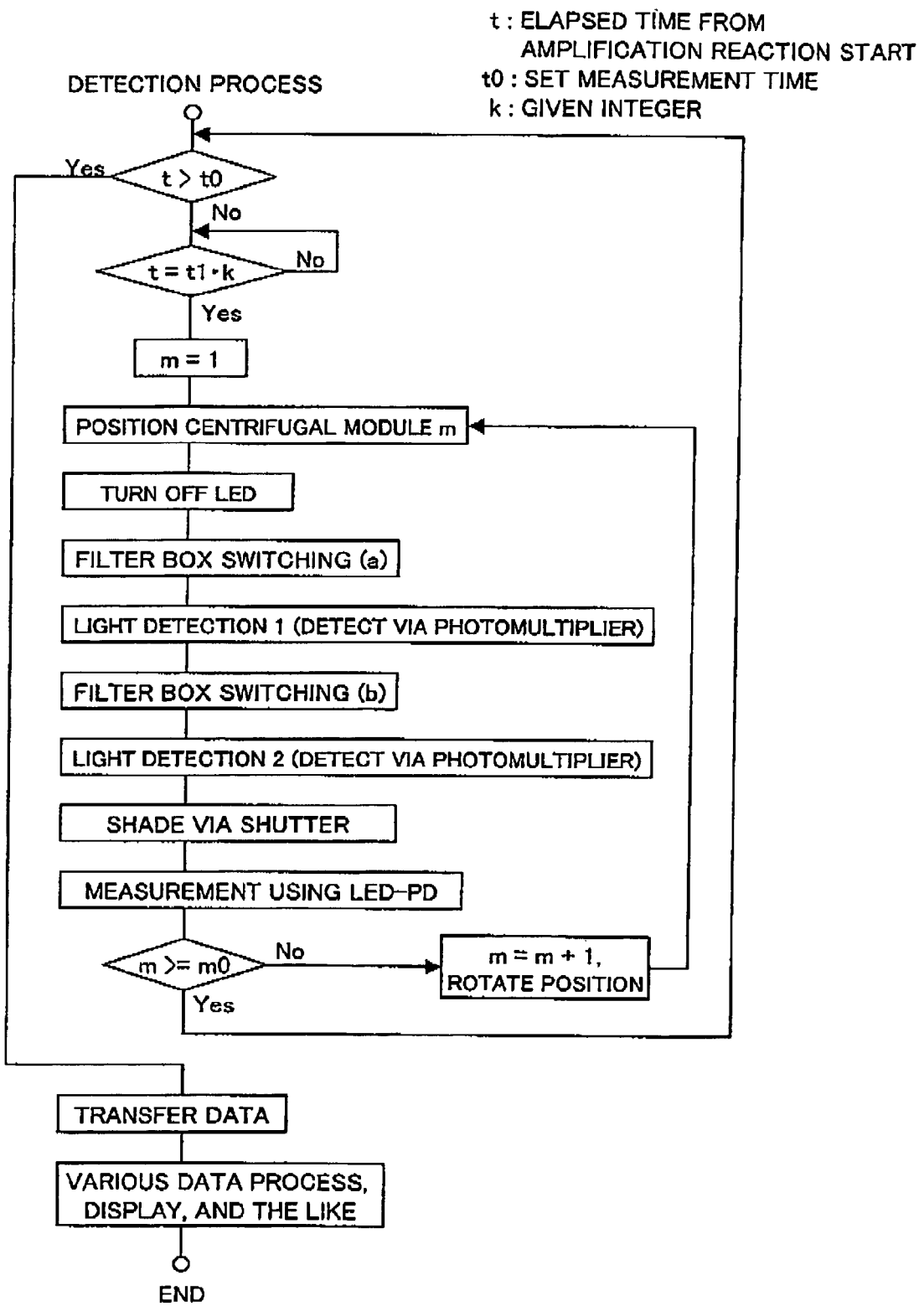
FIG. 12 shows a flow diagram of a detection process in embodiment 2.

FIG. 12 shows a flow diagram of a detection process procedure in the present embodiment. A light irradiation process using LED is added to the procedure of embodiment 1. Because of the presence of two types of optical systems, a process for blocking an LED light before the measurement using the photomultiplier and a process for blocking a light emitted from a light source 20 before LED measurement are added so as to prevent each light from affecting each other.

Embodiment 3

Figure 13:
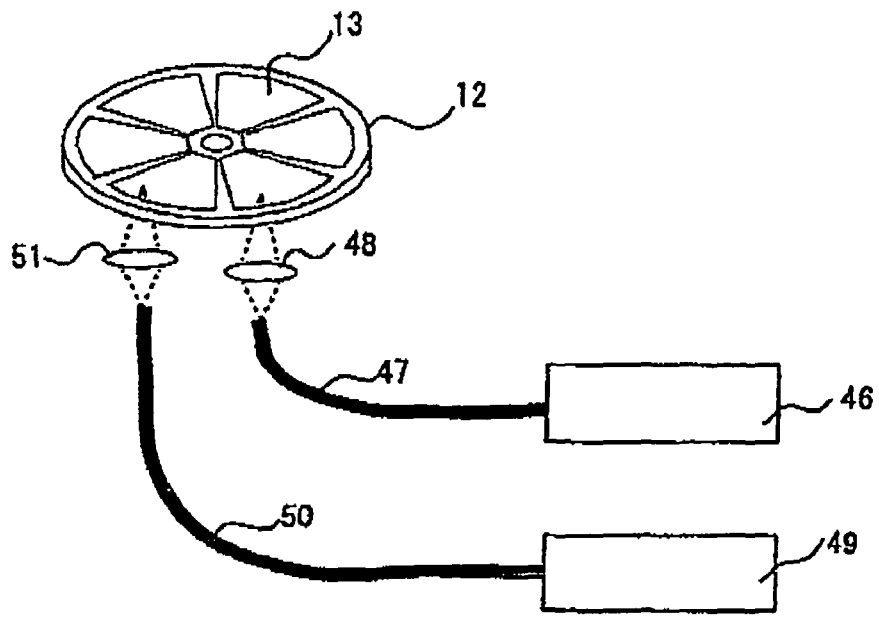
FIG. 13 shows a configuration diagram of an optical detection portion of embodiment 3.
Figure 14:
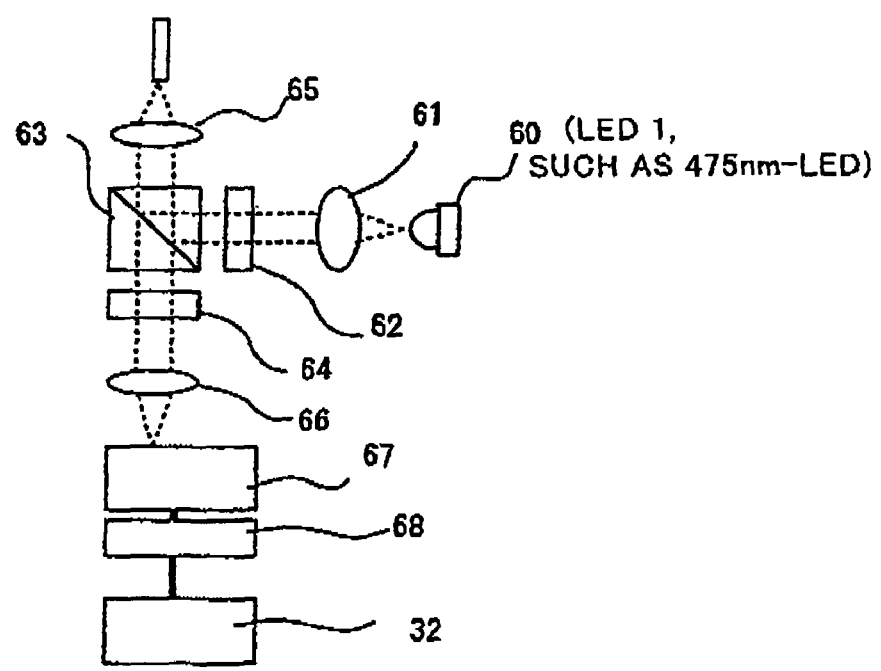
FIG. 14 shows a configuration diagram of a light detection unit of embodiment 3.
Figure 15:
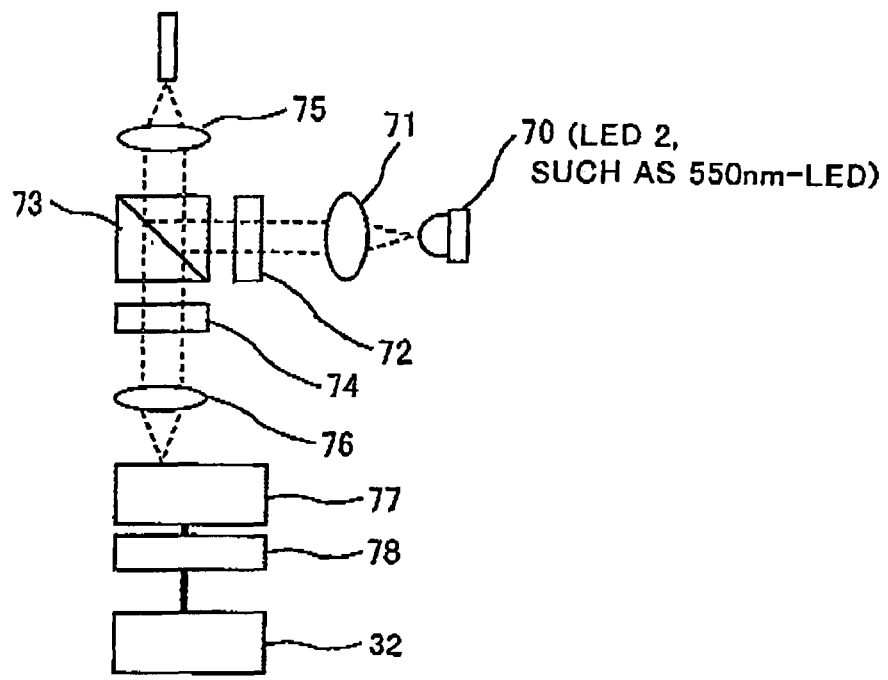
FIG. 15 shows a configuration diagram of the light detection unit according to another example of embodiment 3.

FIG. 13 shows a configuration diagram of another optical detection portion regarding the analytical apparatus using the method for detecting a biological-related substance. Light detection units are disposed, by which two types of fluorophores are independently detected when they are used. A light detection unit 46 irradiates and detects the portion for light detection (extraction/detection port) in a certain centrifugal module via an optical fiber 47 and a lens 48. Another light detection unit 49 irradiates and detects the portion for light detection (extraction/detection port) in another centrifugal module via an optical fiber 50 and a lens 51. FIGS. 14 and 15 show configuration diagrams of the light detection units 46 and 49. The light detection unit 46 responds to a fluorophore FAM® and a blue LED having a central wavelength of 475 nm is used as an excitation light source 60.

An LED light is introduced into the optical fiber 47 (NA=0.22, core diameter: 400 µm) through a lens 61, a monochromatization filter 62 for excitation lighting, a dichroic mirror block 63, and an objective lens 65. Fluorescence received via the optical fiber, for example, is collimated again via the objective lens 65 and a necessary light component is selected via the dichroic mirror block 63 and an optical cut filter 64 for fluorescence detection. The light component is condensed via a lens 66. A spectroscope 67 and a CCD line sensor 68 are used. The intensity of light divided by wavelength is measured and data thereof is transmitted to the control unit 32.

The light detection unit 49 responds to a fluorophore ROX® and a green LED having a central wavelength of 550 nm is used as an excitation light source 70. An LED light is introduced into the optical fiber 50 (NA=0.22, core diameter: 400 µm) through a lens 71, a monochromatization filter 72 for excitation lighting, a dichroic mirror block 73, and an objective lens 75. Fluorescence received via the optical fiber, for example, is collimated again via the objective lens 75 and a necessary light component is selected via the dichroic mirror block 73 and an optical cut filter 74 for fluorescence detection. The light component is condensed via a lens 76. A spectroscope 77 and a CCD line sensor 78 are used. The intensity of light divided by wavelength is measured and data thereof is transmitted to the control unit 32.

The measurement of scattered light is conducted in the same manner as in embodiment 1. In the present example, when a plurality of fluorophores are detected, time loss resulting from the switching of filters can be reduced, enabling measurement with an improved signal-to-noise ratio. Since the switching of filters is unnecessary, continuous measurement becomes possible in which, while the holder 12 of the centrifugal modules is rotated at a constant speed, light is detected when the centrifugal modules return to predetermined positions. This enables mechanically stable measurement with easy operations, as compared with a method where the rotation and stop is repeated.

Embodiment 4

Figure 16:
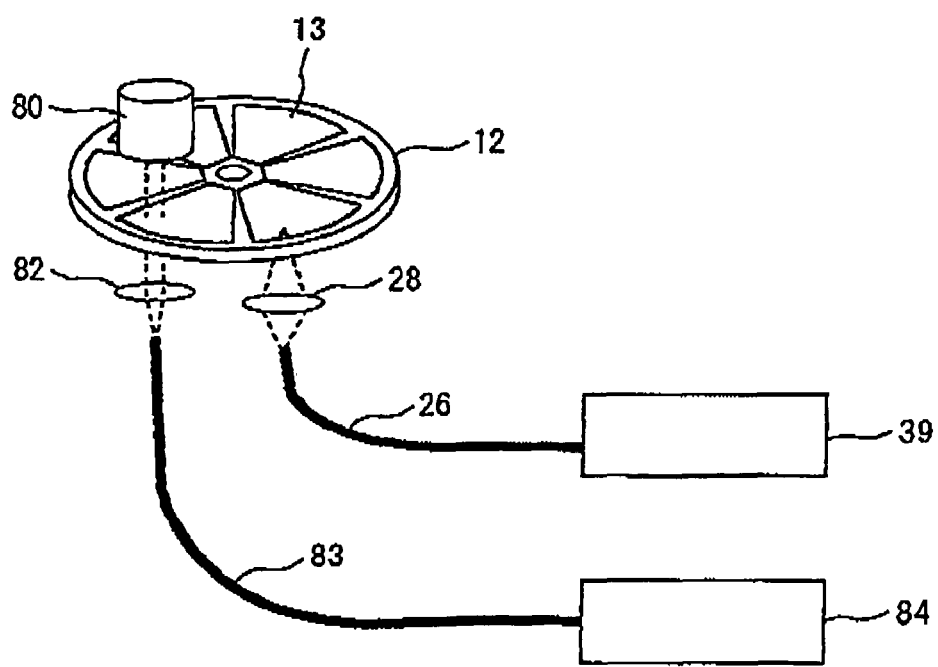
FIG. 16 shows a configuration diagram of an optical detection portion of embodiment 4.

A method for judging the state of a measurement solution using the absorption of light rather than the scattering of light is described. A dye solution different from a solution for fluorophore-labeling and having no effect on fluorescence measurement is added to a reagent for detecting an amplification reaction, and the amplification reaction is conducted in the same manner as above, thereby measuring the reaction. FIG. 16 shows a configuration diagram of another optical detection portion of the analytical apparatus using the method for detecting a biological-related substance. The light detection unit 39 has the same configuration as in embodiment 2.

Figure 17:
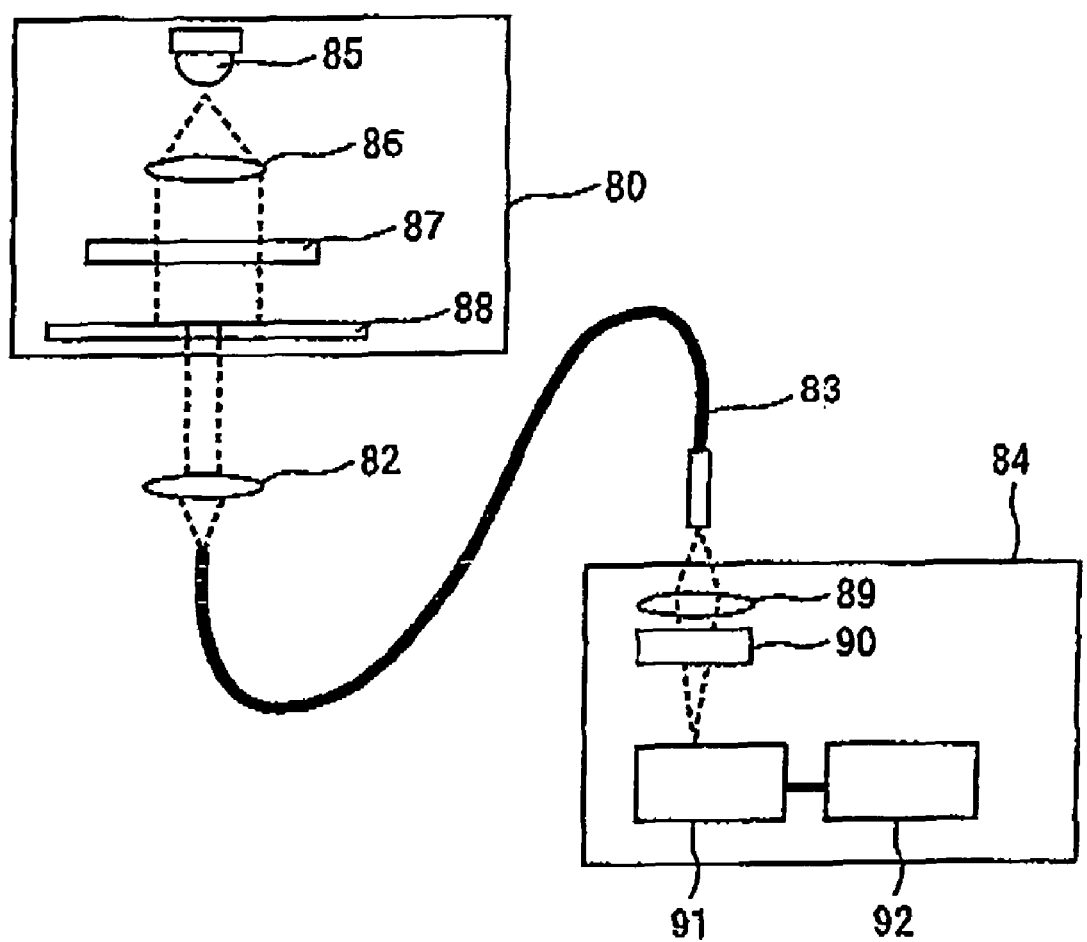
FIG. 17 shows a configuration diagram of a light detection unit of embodiment 4.

The portion for light detection (extraction/detection port) of a certain centrifugal module 13 is irradiated via the optical fiber 26 and the lens 28, and fluorescence is detected in the same manner as in embodiment 2. Further, another light source unit 80, lens 82, optical fiber 83 and light detection unit 84 are prepared, and information on the portion for light detection (extraction/detection port) of a centrifugal module in another position is obtained. FIG. 17 shows a configuration diagram of the light detection unit. The light detection unit 80 forms a beam of light by finely collimating a light of a lamp 85 via a lens 86, a monochromatic optical filter 87, and a slit 88. The light detection unit 80 irradiates the finely collimated beam of light onto a measurement solution inside the portion for light detection (extraction/detection port) of the centrifugal module, condenses transmitted light thereof via the lens 82, and introduces the transmitted light into the light detection unit 84 through the optical fiber. Further, the intensity of the transmitted light is detected via a light detector through a lens 89 and an ND filter 90, converted from analog to digital, and then transmitted to the control unit.

Although the wavelength of the monochromatic optical filter desirably includes a wavelength such that the added dye indicates the absorption maximum, the wavelength is not especially limited so long as a wavelength is absorbed by the added dye. Accordingly, when the fluid volume is reduced due to evaporation, for example, or the liquid is shifted, the intensity of the transmitted light is increased. When air bubbles are generated, for example, the intensity of the transmitted light is decreased due to scattering. By thus monitoring the change of the intensity of the transmitted light, the state of the liquid can be understood, thereby detecting abnormality.

Figure 18:
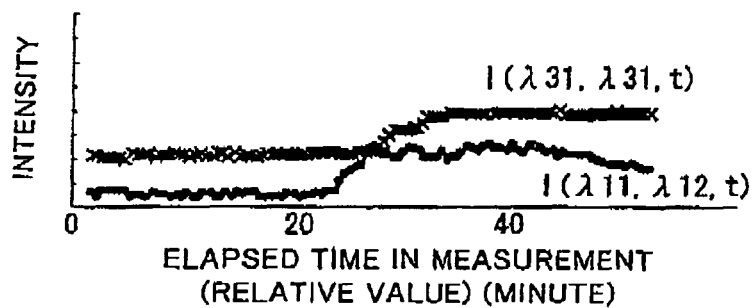
FIGS. 18A-18C show graphs of an example of a light detection result in embodiment 4.
Figure 18:
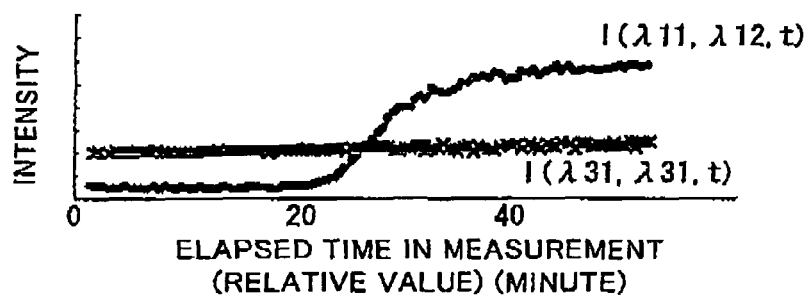
Figure 18:
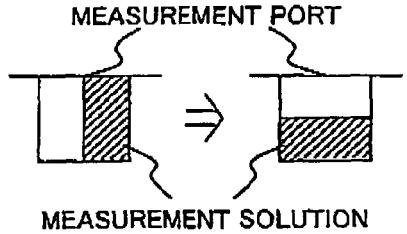

An example of a light detection result obtained by the above operations is described. FIGS. 18A-18C shows only those signals extracted from a given centrifugal module, indicating time change. I ($\lambda 11$, $\lambda 12$, t) shows a target component of a fluorescence wavelength, and I ($\lambda 31$, $\lambda 31$, t) shows the intensity of a transmitted light from a measurement solution. FIG. 18B shows a change in a normal measurement case, in which an amplification reaction is caused with the passage of time, and fluorescence is increased. In this case, the intensity of transmitted light is almost unchanged. In contrast, FIG. 18A shows the passage of time regarding a light detection result in the case where measured values are abnormal.

FIG. 18A shows an increase of the intensity of the transmitted light during am amplification reaction, in which the measurement solution is shifted and the thickness of the liquid is changed. Consequently, the fluorescence intensity changes such that it is seemingly decreasing. In this manner, by simultaneously monitoring the intensity of the transmitted light, the abnormality of the reaction liquid can be detected, and erroneous results can be prevented, thereby improving detection accuracy. Especially, the fluid volume can be directly monitored and quantified, so that an accurate judgment can be made. FIG. 18C illustrates the abnormal state of FIG. 18A, where the liquid in the port unevenly positioned by centrifugal force as shown in the left drawing is dropped to the bottom of the port during measurement, so that measurement conditions are changed.

Embodiment 5

Figure 19:
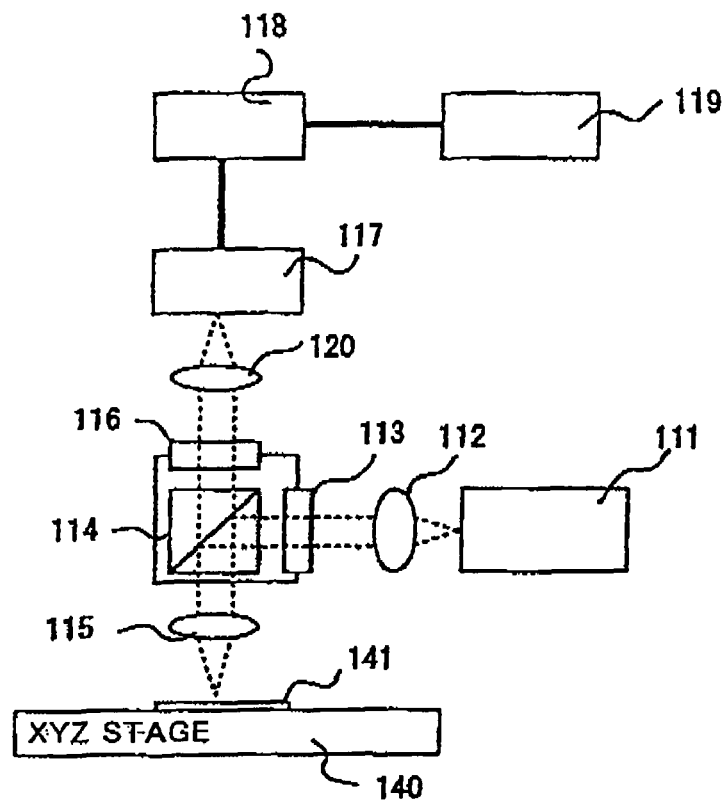
FIG. 19 shows a configuration diagram of a fluorescence measurement apparatus of embodiment 5.

Fluorescence measurement of a DNA microarray is described. FIG. 19 shows a configuration diagram of a fluorescence measurement apparatus of the present embodiment. In the same manner as in embodiment 1, a light from an excitation light source 111, such as a laser light source, a mercury lamp, or the like, is irradiated onto a DNA microarray 141 held in an XYZ stage 140 through a lens 112, a monochromatization filter 113 for excitation lighting, a dichroic mirror block 114, and an objective lens 115. A generated fluorescence is condensed via the objective lens 115 again and is injected into a spectroscope 117 through the dichroic mirror block 114 and a cut filter 116 for fluorescence measurement.

Figure 20:
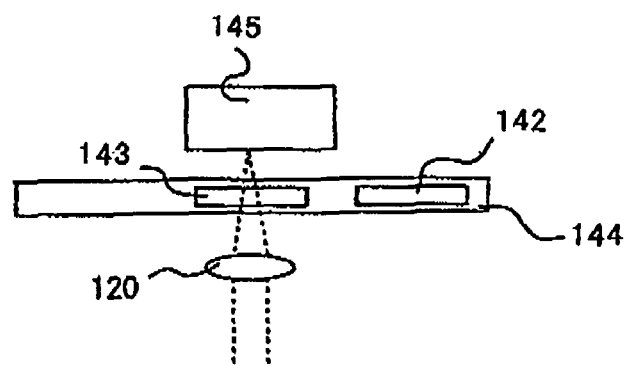
FIG. 20 shows a configuration diagram of another main portion of the fluorescence measurement apparatus of embodiment 5.

The light injected into spectroscope 117 is transformed into spectra and detected via a CCD line sensor 118. The intensity thereof is transmitted to a data processing unit 119, and then processed. The DNA microarray 141 is scanned on the XYZ stage 140. An excitation light may be scanned. Detection may also be conducted using a two-dimensional camera. In this case, the portions of the cut filter 116 for fluorescence measurement, the spectroscope 117, and the CCD line sensor 118 are changed as shown in FIG. 20. In other words, they are changed to a filter 142 for detecting a component of an excitation wavelength, a filter changer 144 for holding a filter 143 for measuring a component of a wavelength regarding a fluorophore, and a two-dimensional cooled CCD camera 145. By detecting an image of the evenly lighted (not shown in the drawings) DNA microarray 141 using the two types of filters in an alternate manner, the intensity of the component of the excitation wavelength may be judged per pixel.

In the present embodiment, in the case where the substrate of the microarray has a flaw, for example, the same effects as in embodiment 1 can be obtained. In the fluorescence measurement using the microarray, the attachment of dust may pose a great problem. Since the fluorescence intensity of a portion where dust is attached does not show an accurate value, signals of the portion are generally removed from a measured value. The distribution of the signal intensity of the dust-attached portion and the distribution of the signal intensity of a portion without dust can be distinguished statistically, so that the removal becomes possible.

However, in the case where the spot area of the microarray is as small as about 10 microns, the number of pixels in the spot is reduced, so that signals cannot be distinguished. Even in this case, in the present example, abnormal pixels can be judged in accordance with the intensity of the component of the excitation wavelength, thereby improving measurement accuracy.

Embodiment 6

A method for judging the state of a measurement solution by detecting at a plurality of positions thereof is described. In the same manner as in embodiment 4, a dye solution different from a solution for fluorophore-labeling and having no effect on fluorescence measurement is added to a reagent for detecting an amplification reaction, and fluorescence measurement is conducted. This is also operable in the detection of scattered light in the same manner.

Figure 22:
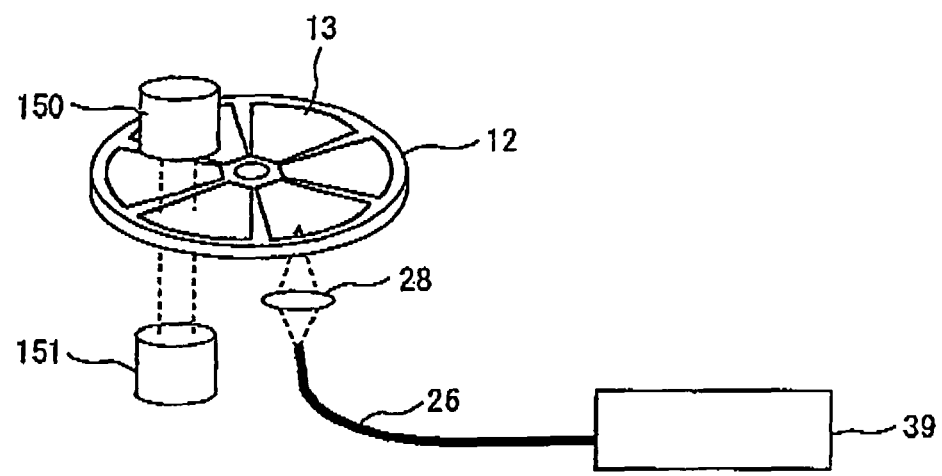
FIG. 22 schematically shows a configuration of an optical detection portion of embodiment 6.

FIG. 22 shows a configuration diagram of another optical detection portion of the analytical apparatus using the method for detecting a biological-related substance. The light detection unit 39 has the same configuration as in embodiment 4. The portion for light detection (extraction/detection port) of a certain centrifugal module 13 is irradiated via the optical fiber 26 and the lens 28, and fluorescence is detected in the same manner as in embodiment 4.

Further, in order to detect the state of the sample solution 5 in the portion 3 for light detection (extraction/detection port) of the centrifugal module, a light source unit 150 and a light detection unit 151 are disposed. In the figure, in consideration of the disposition of the optical unit, the detection is conducted in the position of a centrifugal module adjacent to a centrifugal module whose fluorescence is detected. The detection may be conducted in any positions, since all centrifugal modules are measured in order by rotating the holder disk 12 such that measurement results of fluorescence intensities, results of state detection regarding the sample solution, and the centrifugal module numbers are corresponded.

Figure 23:
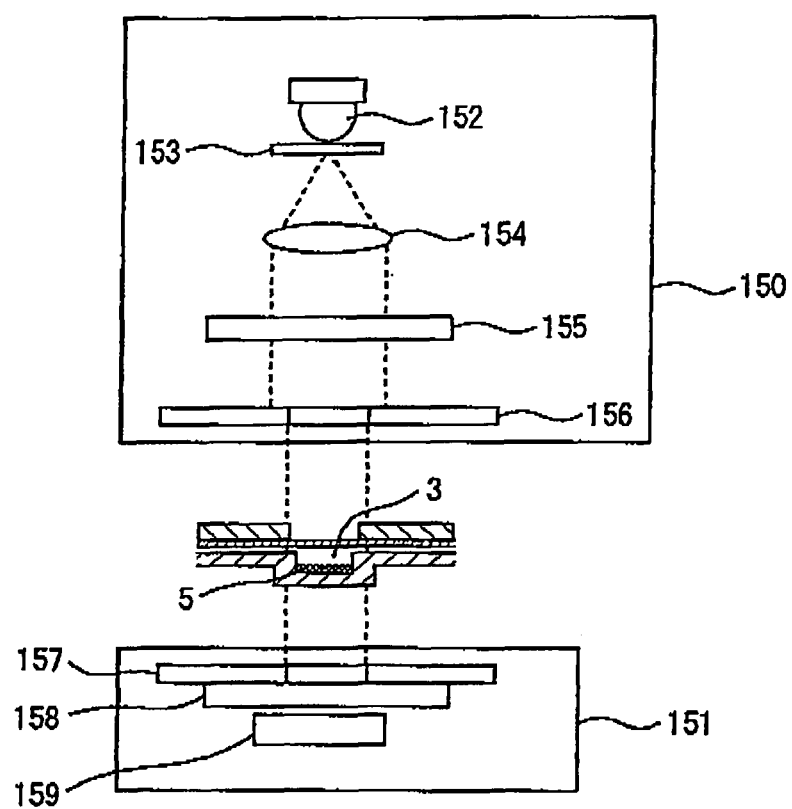
FIG. 23 shows a configuration diagram of a light source unit and a detection unit of embodiment 6.

FIG. 23 shows a configuration diagram of the light source unit 150 and the detection unit 151. The light source unit 150 comprises a lamp 152, a pinhole 153, a lens 154, a monochromatic optical filter 155, and an aperture 156. The light source unit 150 forms a monochromatic light collimated to a size of the portion 3 for light detection of the centrifugal module or to a size somewhat larger than the portion 3 for light detection and irradiates the monochromatic light onto the portion 3 for light detection.

A light transmitted through the measurement solution 5 in the portion for light detection is received via the detection unit 151. In other words, the transmitted light is detected via an aperture 157, a monochromatic optical filter 158, and two-dimensional area sensor 159, converted from analog to digital, and then transmitted to the control unit.

Although the wavelength of the monochromatic optical filter desirably includes a wavelength such that an added dye indicates the absorption maximum, the wavelength is not especially limited so long as a wavelength is absorbed by the added dye. When the fluid volume is reduced due to evaporation, for example, or the liquid is shifted, the intensity of the transmitted light is increased, When air bubbles are generated, for example, the intensity of the transmitted light is decreased due to scattering. By thus monitoring the change of the intensity of the transmitted light, the state of the liquid can be understood, thereby detecting abnormality.

In accordance with the present structure, the light intensity in a given position in the portion 3 for light detection is detected, the transmittance of the position is determined, and the fluid volume is estimated. Thus, the distribution of a liquid in the portion 3 for light detection, the unevenness of the liquid, and the reduction of the fluid volume due to the evaporation of the liquid, for example, can be judged. In the case of the reduction of the fluid volume, by displaying the alert message "Detection volume error", for example, on the measurement screen of the controller PC as described in embodiment 1, the abnormality of a reaction liquid can be detected, and erroneous results can be prevented, thereby improving detection accuracy. Especially, the fluid volume can be directly monitored and quantified, so that an accurate judgment can be made.

Also, regarding the unevenness of the liquid, erroneous results can be prevented by performing the same display.

The structures of the light source unit 150 and the detection unit 151 can also be realized in the same manner by monochromatizing a plain emission type light using a filter, imaging and irradiating the plain emission type light in the portion for light detection of the centrifugal module, and imaging and detecting the image of the portion for light detection in the two-dimensional area sensor through the filter, in addition to the aforementioned structure. Further, the structures can be realized by disposing a line sensor or a plurality of light detectors in an imaging position such that an image of a necessary position in the portion for light detection can be obtained instead of using the two-dimensional area sensor.

Also, the reduction of the liquid and the state of dewdrops can be judged by detecting scattered light and the angular dependence of the scattered light in a plurality of positions instead of receiving a transmitted light in the plurality of positions, so that erroneous results can be prevented.

What is claimed is:

1. A method for detecting a target biological-related substance, comprising the steps of:
    (a) labeling a biological-related substance using a fluorophore,
    (b) capturing the biological-related substance in a portion for light detection,
    (c) irradiating an excitation light for exciting the fluorophore onto the portion for light detection,
    (d) detecting a light emitted by the portion for light detection after dividing the light into a plurality of wavelength zones, wherein one of the plurality of wavelength zones is substantially the same as that of a wavelength component of the excitation light,
    (e) simultaneously monitoring an intensity of the component of the excitation light wavelength and the intensity of the light emitted by the fluorophore,
    (f) comparing the light intensity of the wavelength zone that is substantially the same as that of the component of the excitation light with a predetermined intensity range obtained from a normal sample,
    (g) quantifying the target biological-related substance, and,
    (h) in the case where the light intensity of the wavelength zone that is substantially the same as that of the component of the excitation light exceeds the predetermined intensity range, judging that the light intensity emitted by the fluorophore in the portion for light detection is not appropriate,
    (i) in the case where the light intensity of the wavelength zone that is substantially the same as that of the component of the excitation light does not exceed the predetermined intensity range, correcting the light intensity emitted by the fluorophore using the light intensity of the wavelength zone that is substantially the same as that of the component of the excitation light.

2. The method for detecting a biological-related substance according to claim 1, wherein in the case where the light intensity of the wavelength zone that is substantially the same as that of the component of the excitation light exceeds the predetermined intensity range, judging and displaying in real time that the fluorescence measurement in the portion for light detection is not appropriate.

3. The method for detecting a biological-related substance according to claim 1, wherein the portion for light detection comprises a region for reaction formed on a substantially planar substrate surface.

4. The method for detecting a biological-related substance according to claim 1, wherein a light detection is conducted in the portion for light detection after an amplification reaction is conducted or along with the amplification reaction.

5. The method for detecting a biological-related substance according to claim 1, wherein a biological sample is carried on any one of a DNA chip, a DNA microarray, or a protein chip.

6. The method for detecting a biological-related substance according to claim 1, wherein the biological sample is carried on a well of a microplate.

7. The method for detecting a biological-related substance according to claim 1, wherein the biological-related substance is labeled with a plurality of types of fluorophores.

8. The method for detecting a biological-related substance according to claim 1, wherein the state of a sample solution is judged by detecting the scattered of light from the sample solution.

9. A method for detecting a biological-related substance, comprising:
    (a) labeling a biological-related substance or such a substance that is substantially the same as the biological-related substance using a fluorophore,
    (b) adding a dye having a main absorption band in the wavelength zone which is different from that of the fluorophore,
    (c) capturing the biological-related substance in a portion for light detection;
    (d) irradiating an excitation light for exciting the fluorophore onto the portion for light detection, and another light to detect the absorption level of the dye,
    (e) detecting a light emitted by the portion for light detection after dividing the light into a plurality of wavelength zones, wherein one of the plurality of wavelength zones is substantially the same as that of a wavelength component of the another light,
    (f) simultaneously monitoring an intensity of the component of the another light wavelength and the intensity of the light emitted by the fluorophore,
    (g) comparing the light intensity of the wavelength zone that is substantially the same as that of the component of the another light with a predetermined intensity range obtained from a normal sample;
    (h) quantifying the biological-related substance or such a substance that is substantially the same as the biological-related substance; and,
    (i) in the case where the light intensity of the wavelength zone that is substantially the same as that of the component of the another light exceeds the predetermined intensity range, judging that the light intensity emitted by the fluorophore in the portion for light detection is not appropriate,
    (j) in the case where the light intensity of the wavelength zone that is substantially the same as that of the component of the another light does not exceed the predetermined intensity range, correcting the light intensity emitted by the fluorescence using the light intensity of the wavelength zone that is substantially the same as that of the component of the another light.

10. The method for detecting a biological-related substance according to claim 9, wherein the portion for light detection comprises a region for reaction formed on a substantially planar substrate surface.

11. The method for detecting a biological-related substance according to claim 9, wherein a light detection is conducted in the portion for light detection after an amplification reaction is conducted or along with the amplification reaction.

12. The method for detecting a biological-related substance according to claim 9, wherein a biological sample is carried on any one of a DNA chip, a DNA microarray, or a protein chip.

13. The method for detecting a biological-related substance according to claim 9, wherein the biological sample is carried on a well of a microplate.

14. The method for detecting a biological-related substance according to claim 9, wherein the state of a sample solution is judged by detecting the transmitted light from the sample solution.

15. The method for detecting a biological-related substance according to claim 9, wherein a dye solution having no effect on fluorescence measurement is added to a sample solution.

16. The method for detecting a biological-related substance according to claim 9, wherein the biological-related substance is labeled with a plurality of types of fluorophores.

* * * * *